(12) United States Patent
Schermer et al.

(10) Patent No.: US 7,233,391 B2
(45) Date of Patent: Jun. 19, 2007

(54) OPTICAL DEVICE INTEGRATED WITH WELL

(75) Inventors: Mack J. Schermer, Belmont, MA (US); Carl Brian Candiloro, Hudson, MA (US)

(73) Assignee: PerkinElmer LAS, Inc., Boston, MA (US)

( * ) Notice: Subject to any disclaimer, the term of this patent is extended or adjusted under 35 U.S.C. 154(b) by 0 days.

(21) Appl. No.: 10/987,593

(22) Filed: Nov. 12, 2004

(65) Prior Publication Data

US 2005/0110989 A1    May 26, 2005

Related U.S. Application Data

(60) Provisional application No. 60/481,688, filed on Nov. 21, 2003, provisional application No. 60/481,732, filed on Dec. 2, 2003, provisional application No. 60/481,874, filed on Jan. 9, 2004.

(51) Int. Cl.
G01N 1/00   (2006.01)
G01N 21/55  (2006.01)

(52) U.S. Cl. .................. 356/246; 356/128; 356/137

(58) Field of Classification Search ............... 356/244, 356/246, 128–113, 445–448; 250/458.1, 250/459.1, 461.1, 461.2; 422/82.08, 82.11
See application file for complete search history.

(56) References Cited

U.S. PATENT DOCUMENTS

| | | | | |
|---|---|---|---|---|
| 4,451,147 A | * | 5/1984 | Dobes et al. | 356/135 |
| 4,580,895 A | * | 4/1986 | Patel | 356/128 |
| 4,640,616 A | | 2/1987 | Michalik | |
| 4,815,843 A | | 3/1989 | Tiefenthaler et al. | |
| 4,844,613 A | | 7/1989 | Batchelder et al. | |
| 4,889,427 A | * | 12/1989 | Van Veen et al. | 356/445 |
| 4,997,278 A | * | 3/1991 | Finlan et al. | 356/128 |
| 5,319,436 A | * | 6/1994 | Manns et al. | 356/246 |
| 5,341,215 A | * | 8/1994 | Seher | 356/445 |
| 5,351,127 A | * | 9/1994 | King et al. | 356/445 |
| 5,623,561 A | | 4/1997 | Hartman | |
| 5,633,724 A | * | 5/1997 | King et al. | 356/445 |
| 5,738,825 A | * | 4/1998 | Rudigier et al. | 422/82.11 |
| 5,815,278 A | * | 9/1998 | Johnston et al. | 356/445 |
| 5,926,284 A | * | 7/1999 | Naya et al. | 356/445 |
| 5,991,488 A | * | 11/1999 | Salamon et al. | 385/129 |
| 6,239,876 B1 | | 5/2001 | Brandenburg | |
| 6,330,062 B1 | * | 12/2001 | Corn et al. | 356/445 |
| 6,335,793 B1 | | 1/2002 | Freeman et al. | |
| 6,396,576 B1 | | 5/2002 | Bleyle | |
| 6,462,809 B1 | | 10/2002 | Ryan et al. | |

(Continued)

FOREIGN PATENT DOCUMENTS

JP    11304693 A  *  11/1999

(Continued)

Primary Examiner—Sang H. Nguyen
(74) Attorney, Agent, or Firm—John F. McKenna; Cesari & McKenna, LLP

(57) ABSTRACT

Methods and systems are disclosed that include an optical device for providing information about one or more samples. The system includes well(s) for holding the sample(s), and in one embodiment, the optical device(s) have non-parallel sidewalls optically contacting the well(s) for providing the information about the sample(s) in the well(s). In some embodiments the optical devices may be truncated prism(s). In some embodiments the optical devices are part of a unibody structure with the well(s).

10 Claims, 14 Drawing Sheets

U.S. PATENT DOCUMENTS

| | | | |
|---|---|---|---|
| 6,594,011 B1 * | 7/2003 | Kempen | 356/369 |
| 6,692,974 B2 * | 2/2004 | Perkins | 436/518 |
| 6,697,158 B2 * | 2/2004 | Ogura et al. | 356/445 |
| 6,734,956 B2 * | 5/2004 | Byrne et al. | 356/128 |
| 6,791,691 B2 * | 9/2004 | Ohtsuka et al. | 356/445 |
| 6,801,317 B2 | 10/2004 | Hofmann | |
| 6,862,094 B2 * | 3/2005 | Johansen | 356/445 |
| 6,864,984 B2 * | 3/2005 | Naya et al. | 356/445 |
| 7,030,988 B2 * | 4/2006 | Kubo et al. | 356/445 |
| 7,064,837 B2 * | 6/2006 | Mori et al. | 356/445 |
| 2003/0026891 A1 | 2/2003 | Qui et al. | |
| 2003/0112427 A1 | 6/2003 | Ryan et al. | |

FOREIGN PATENT DOCUMENTS

| | | |
|---|---|---|
| WO | WO 98/46981 | 4/1998 |
| WO | WO 01/86262 A1 | 5/2001 |

* cited by examiner

OPTICAL DEVICE INTEGRATED WITH WELL

RELATED APPLICATIONS

This application claims the benefit of Provisional Patent Applications 60/481,688 filed on Nov. 21, 2003, Ser. No. 60/481,732 filed on Dec. 2, 2003, and Ser. No. 60/481,874 filed on Jan. 9, 2004, the contents of all of which are expressly incorporated herein by reference in their entireties.

FIELD

This patent application generally relates to an optical device contacting a well for detecting a reaction in a sample in the well.

BACKGROUND

Optical techniques, including prism refractometry, interferometry, and surface plasmon resonance (SPR), have long been used for measuring optical properties of samples, such as index of refraction.

Refractometers have been used in the field of analytical chemistry for measuring the index of refraction of liquids for analytical purposes. Modern automatic refractometers determine the critical angle between transmission and total internal reflection in an optical prism of known high refractive index. At the interface between a liquid sample and a higher index prism, the critical angle $\theta_{crit}$ is defined by $\sin(\theta_{crit}) = n_{low}/n_{high}$, where $n_{high}$ is the refractive index of the prism and $n_{low}$ is the index of the liquid being measured. With knowledge of the refractive index of the prism, by measuring the critical angle, the index of the liquid being measured can be calculated.

Waveguide interferometry, which can measure very small shifts in interference patterns generated by minute changes in refractive index, is inherently more sensitive than prism refractometry. However, the waveguide interface to the sample is also inherently more expensive.

SPR takes advantage of the fact that at a unique narrow range of angles, a thin layer of metal does not reflect light as well as it does at other angles. In this narrow range of angles, energy is transferred from light rays striking the metal into the metal itself. The energy is transferred into the metal instead of being reflected because of the surface plasmon resonance effect. The pronounced reduction in reflection occurring at that narrow range of angles produces an attenuated band within an otherwise bright region of reflected light that shines on a detector. The narrow range of angles depends on index of refraction of a material that is on the opposite surface of the thin metal. Thus, a chemical reaction in a material on that opposite surface that changes its index can result in a shift in the narrow range of angles. This shift can be detected, providing a way to determine that a reaction occurred or to follow the reaction dynamically.

While each of these systems has been studied and used, all remain complex and expensive to use, require complex handling of materials, provide contamination issues, have required careful preparation, and/or present challenges for uses demanding high throughput.

SUMMARY

An optical device for providing information about multiple samples includes a structure that has multiple wells for holding the samples, and at least one optical device having nonparallel sidewalls optically contacts the wells for providing the information about the samples in the wells.

In one embodiment, the structure includes a microplate. In one embodiment, the optical device includes a measuring surface that forms a bottom surface of the wells. In one embodiment, this bottom surface includes a coating that can include a polymeric layer a metal layer, and/or a polymeric layer on the metal layer.

In one embodiment the optical device comprises a truncated prism that can include an irregular trapezoid prism.

One embodiment includes a plurality of the optical devices, and one of the optical devices contacts each well of the structure.

In one example, the structure includes n wells arranged in a two-dimensional array wherein one of the optical devices optically contacts an integer factor of the n wells.

In one embodiment, the plurality of wells and the at least one optical device are integral parts of a unibody construction that may be fabricated of a polymeric material. The polymeric material can include at least one from the group including polystyrene, polycarbonate, polysulfone, and polymethylmethacrylate. The unibody construction may be fabricated from an injection molded polymeric material.

A light source and a detector can also be included. A plurality of light sources and detectors can be arranged for measuring a well of the structure. The light source can include at least one from the group including a laser, an LED, an SLD, and a bulb. The detector can include a CCD or a CMOS array.

In one embodiment the sidewalls are substantially planar.

Also disclosed is an optical device for providing information about a plurality of samples, comprising a unibody construction including a plurality of wells for holding the plurality of samples, and at least one non-planar optical device integrally connected with the plurality of wells in the unibody construction for providing the information about the plurality of samples in the plurality of wells.

In one embodiment, the unibody construction comprises a microplate. The wells can include a bottom surface having a coating. The coating can include a polymeric layer, a metal layer, and/or a polymeric layer on the metal layer.

The optical device can include a truncated prism that can include an irregular trapezoid prism.

One embodiment includes a plurality of the optical devices, and a single one of the optical devices is integrally connected with only one well of the construction.

The unibody construction can include n wells arranged in a two-dimensional array wherein the at least one optical device is integrally connected to an integer factor of the n wells.

In one aspect the unibody construction is fabricated of a polymeric material. The polymeric material may include at least one from the group including polystyrene polycarbonate, polysulfone, and polymethylmethacrylate. The unibody construction may be fabricated from an injection molded polymeric material.

One embodiment also includes a light source and a detector. An embodiment includes a plurality of light sources and detectors arranged for measuring a well of the unibody construction. The light source includes at least one from the group including a laser, an LED, an SLD, and a bulb. The detector includes a CCD or a CMOS array. The light source and the detector may be moveable with respect to the unibody construction for sequentially measuring samples in different wells of the unibody construction.

The present teachings also include a method of measuring an optical property of a material, the method including providing a structure and at least one optical device, where the structure includes a plurality of wells, each for holding a material, where the at least one optical device has a first facet, a second facet, and a third facet, the second facet extending between the first facet and the third facet, the first facet being nonparallel with the third facet, and the second facet optically contacting at least one of the plurality of wells. The method further includes providing the material to/in at least one of the wells, shining light on the well(s) through the first facet to provide total internal reflection from the second facet, receiving the totally internally reflected light through the third facet at a detector, and determining information about the material in the well(s) from the light received by the detector.

The method can include providing a metal layer on the second facet. The information can include a change in an optical property resulting from a binding assay.

Also disclosed is a method of measuring an optical property of a material, the method including providing a unibody construction including a plurality of wells and at least one non-planar optical device, where each of the wells is for holding a material, and where the non-planar optical device(s) has a facet integrally connected with the plurality of wells in the unibody construction. The method also includes providing the material in the well(s), shining light on the well(s) so as to strike the facet, receiving light derived from the well(s) at a detector, and determining information about the material in the well from the light received at the detector.

In one embodiment, the unibody construction comprises a microplate. The optical device can include a prism which can be a truncated prism. For the disclosed method, the determining information can include determining a change in an optical property resulting from a binding assay. The determining information can include determining whether a reaction has occurred in the material and/or the extent of the reaction in the material. The determining information can include determining a critical angle and/or a change in a critical angle. The determining information can include determining an index of refraction and/or a change in an index of refraction, a property related to an index of refraction and/or a property related to a change in an index of refraction. The facet can include a coating that may include thin metal. Accordingly, in determining, the method can include using SPR. In some embodiments, the shining can include shining the light on at least one of the wells before shining the light on another of the wells. The receiving can include receiving the light from at least one of the wells before receiving the light from another of the wells.

The present teachings also include a method of processing an image. The method includes providing laser illumination to form an image, transforming the image to a frequency domain, removing high frequency components, and transforming the frequency domain to an image. The transforming can include DCT. The image can include a refractometry image, and the method can include analyzing the refractometry image to determine information about a sample in a well. The well can be part of a microplate. In an embodiment, the image can include an interferometry image.

The methods and systems include an optical device for providing information about a plurality of samples. The device(s) includes a structure having a plurality of wells for holding the plurality of samples. At least one optical device contacts the plurality of wells for providing the information about the plurality of samples in the plurality of wells. The device also includes a reading instrument having components for reading from a prism optical device and components for reading from a grating/waveguide optical device.

The present teachings include a device for measuring a sample. The device includes a well for holding the sample, and a truncated prism that optically contacts the well.

BRIEF DESCRIPTION OF DRAWINGS

FIG. 7a is the raw image as recorded by a CCD array detector; FIG. 7b shows the image of FIG. 7a as transformed by a Discrete Cosine Transform (DCT) process; and FIG. 7c shows the image of FIG. 7b as thresholded after the DCT transform;

FIG. 8a is the raw image as recorded by a CCD array detector; FIG. 8b shows the image of FIG. 8a as transformed by a DCT process; and FIG. 8c shows the image of FIG. 8b as thresholded after the DCT transform;

FIG. 9a is the raw image as recorded by a CCD array detector; FIG. 9b shows the image of FIG. 8a as transformed by a DCT process;

DETAILED DESCRIPTION

Figure 1:
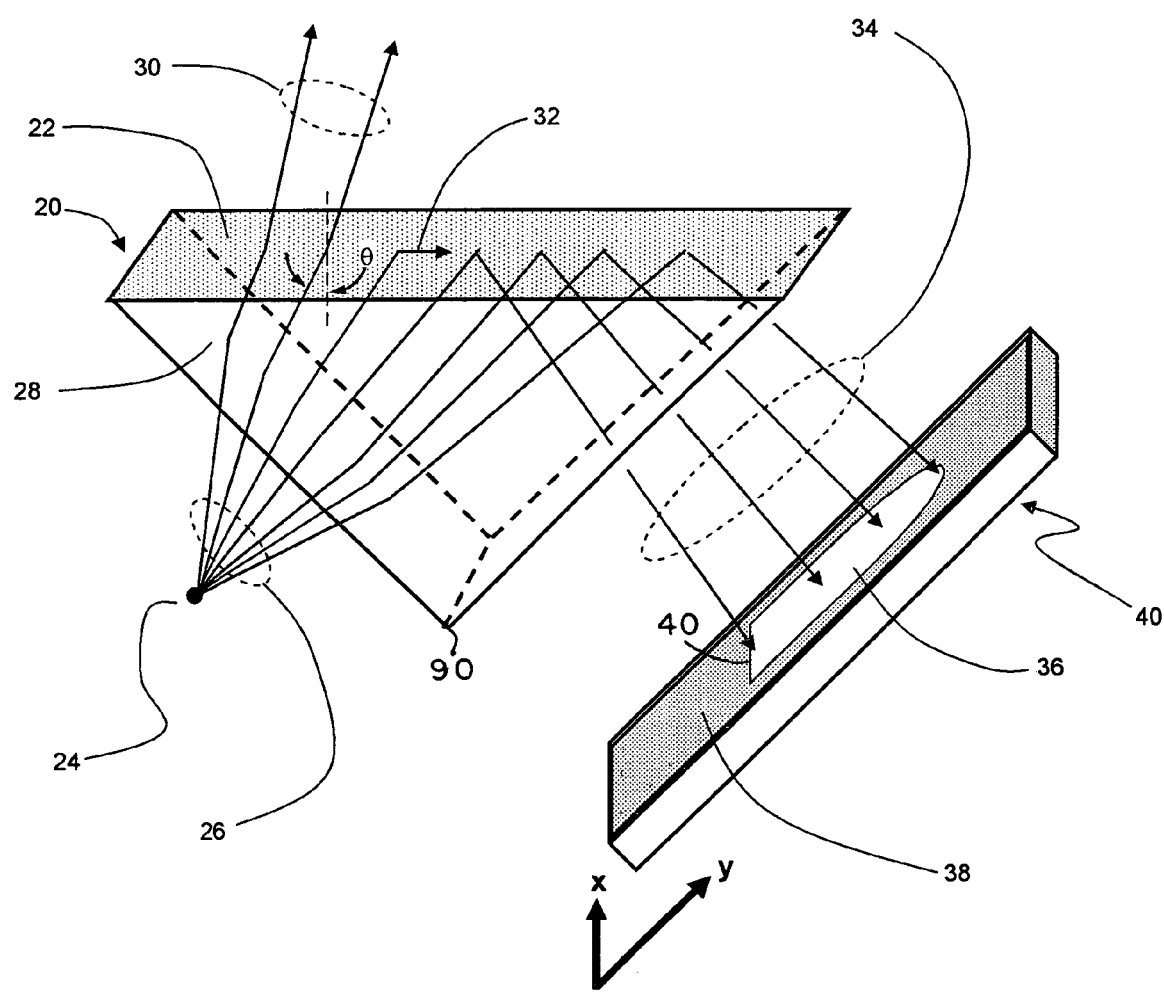
FIG. 1 is a three dimensional optical schematic of a prior-art prism-based automatic refractometer.

Prism refractometry involves applying a liquid on a prism measuring surface and shining a substantially monochromatic fan of light rays on a second prism facet so that the light enters the prism and refracts and reflects from the measuring surface. Rays with low incidence angles to the measuring surface are transmitted. Sufficiently high incidence angle rays are reflected by total internal reflection (TIR). The evanescent wave of the reflected light extends a distance of a fraction of a wavelength into the liquid being measured and interacts with it so that its index determines the critical angle. The TIR reflected rays leave the prism through a third prism facet and strike an array imaging detector, such as a charged-coupled device (CCD). The boundary between total internal reflection and transmission, e.g. the critical angle, defines one edge of the image formed on this detector, and thus the critical angle can be measured by analyzing the image acquired by the CCD. Descriptions of such prism refractometry instruments and analyses are found in U.S. Pat. No. 4,640,616 to Michalik ("the '616 patent") and U.S. Pat. No. 6,396,576 to Bleyle ("the '576 patent"), incorporated herein by reference. The technique can be used to measure bulk liquid properties or thin film liquid properties.

The use of a prism-based automatic refractometer to measure biological assay results was described by Ryan et al. in U.S. Pat. No. 6,462,809 ("the '809 patent") and U.S. Published Application 2003/0112427, incorporated herein by reference. In one use one member of a specific binding pair (e.g. antibody and antigen; single-stranded DNA and its complement, etc.) is immobilized on a solid support, such as a flat plastic disk, so that it is available to capture the other member of the binding pair from a sample solution later placed on the disk. The disk is placed in optical contact with the prism of an automatic refractometer, using an index-matching fluid to facilitate optical contact between the prism and the disk. Then the refractive index of the disk's surface is measured. The measurement can be used to determine the initial index of refraction of the immobilized member and it can later be used again to determine the extent of binding due to the assay.

However, the small flat disks disclosed in the '809 patent are not convenient carriers or vessels for either the immobilized member or the sample later placed on the disk. Also, the index-matching fluid between the assay support and the measuring instrument must be applied consistently with no bubbles or dust before applying the disk to provide consistent results. Also, the disk is often difficult to remove from the prism after the measurement because of surface tension. Finally, the index matching fluid must be cleaned from the instrument and from the disk after the assay to avoid contamination of the next assay sample and the buildup of dust. All of these steps of processing the index matching fluid slow down the measurements and reduce instrument throughput and reliability.

In most modern life science research or drug discovery settings, multiple samples need to be measured in a single session. For this reason, the molded microplate consisting of 96, 384, or 1,536 wells is very commonly used for assays with signal-producing label chemistries, such as fluorescence, luminescence, or radioactivity. Microplates are made to standardized dimensions defined by the Society for Biomolecular Screening (SBS) Microplate Standards specifications SBS-1 through SBS-5, most recently revised in May 2003. A great deal of instrumentation, automation and infrastructure has been accumulated in life science research and drug discovery institutions to accommodate signal producing label chemistry assays in microplates.

Other devices are also known in life science research, such as optical biosensors, which are used for detecting binding of biomolecules without the use of labeling reagents—a technique often called "label-free detection" or "label-less detection." Optical biosensors also use the evanescent light wave by incorporating waveguides in which propagating light experiences many TIR interactions with the surface of the waveguide upon which an assay sample is located. In effect, optical biosensors are refractometers that use thin waveguides instead of prism elements.

Optical biosensors are often fabricated in the form of a planar chip. Light is injected into the waveguide either directly through the ends, as described in U.S. Pat. No. 6,335,793, to Freeman et al. ("the '793 patent"), or more commonly using a grating as a coupler to the waveguide, as described in U.S. Pat. No. 4,815,843 to Tiefenthaler et al., in a chip format, and in U.S. Pat. No. 5,738,825 ("the '825 patent) to Rudigier et al., in a microplate format, all of which are incorporated herein by reference. Refractive index changes are detected by measuring wavelength or coupling angle changes with grating sensors, or interferometrically with dual waveguide sensors. Optical biosensors based on waveguides have been proven to be sensitive assay measurement devices, but have not yet met with widespread use in biological research due to their high cost of manufacture and the complexity of their complementary reading instruments. Waveguides and gratings are manufactured by semiconductor vacuum deposition processes and photolithography processes that result in expensive sensors. Other mechanisms for manufacturing gratings, such as replication, as described in U.S. Published Application 2003/0026891 to Qui et al., incorporated herein by reference, still require vacuum deposition of the waveguide layer. They are also relatively expensive compared to the fabrication methods used for standard assay vessels intended for use with labeled assays, such as injection-molded microplates.

Waveguide optical biosensors using interferometry as the measurement mechanism have also been described, for example in the '793 patent and in U.S. Pat. No. 6,239,876 to Brandenburg ("the '876 patent"), and U.S. Pat. No. 5,623,561 to Hartman, both of which are incorporated herein by reference. Interferometry, which can measure very small shifts in interference patterns generated by minute changes in refractive index, is inherently more sensitive than prism refractometry. However, the waveguide assay carrier is also inherently more expensive. A grating is described to couple interrogation light into a planar waveguide sensor.

The present application provides a system that can be used to measure assay results using microplates using either interferometry or prism refractometry. For applications requiring high sensitivity, the more expensive interferometry microplate can be used while for those applications requiring less sensitivity the low cost refractometry microplate can be used.

Figure 6:
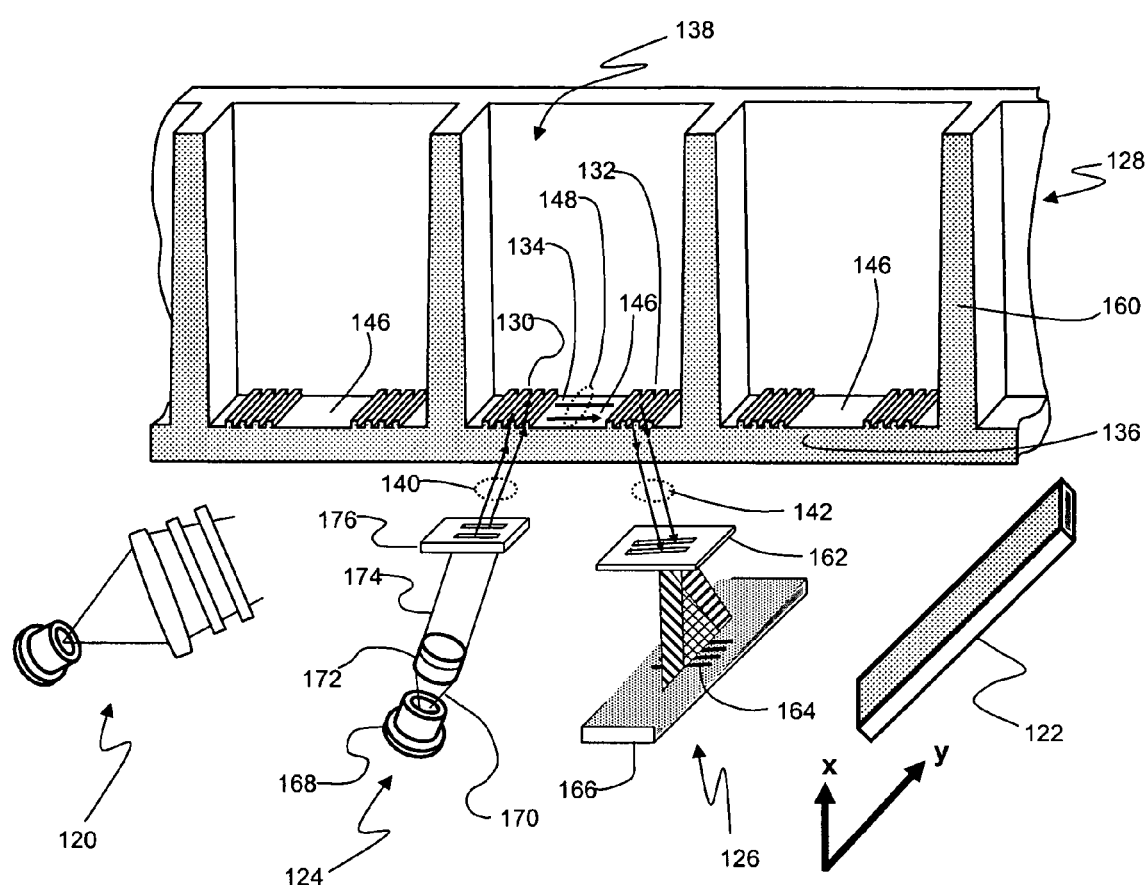
FIG. 6 is a three dimensional view of another embodiment showing an enlarged view of several wells of a microplate manufactured with grating-waveguide interferometry formed in microplate well bottoms contacting the microplate, and with a light source, beam shaping optics, filter, and a CCD array detector in place for either prism refractometry or grating-waveguide interferometry, depending on which microplate is in place.

Light sources and detectors for both types of measurements are provided, as shown in FIG. 6. The microplate with the integral molded prism described in this application can be used for the refractometry measurement. The microplate with an integral prism has a unibody construction if the prism is formed in one piece of material with the wells of the microplate without adhesive there between. The adhesively connected well structures and microplates described in the '825 and '876 patents can be used for the interferometry measurement. One part of the adhesively assembled microplate includes walls of the array of microplate wells with no well bottoms. The other part, including the bottoms of the wells, has the grating and waveguide that may have been photolithographically defined. Either microplate can be provided for measurement in the same instrument. In an embodiment, two light sources are provided, one for each measurement. For the prism refractometer a light source that provides light from a point source can be used. For interferometry, a non-diverging beam can be used.

Analytical refractometers known to date have not been designed with the prism element as a disposable component that would be used only once for one sample. The disposable disks disclosed the '809 patent are illustrative in that the element in contact with an assay sample is disposable, but this system requires the inconvenient and messy use of index-matching fluid to optically couple the disks to a permanent glass prism in the instrument.

Modern mold-making and injection molding processes are capable of making inexpensive optical components en masse; in fact it is routine to mold microplates with flat, transparent bottoms with sufficient optical quality to support laser microscopy and microarray imaging through the molded plastic as provided, for example, for microplates offered by Perkin Elmer, Inc. (Boston, Mass.), Nalge Nunc International (Rochester, N.Y.), Corning Inc. Life Sciences (Acton, Mass.), Whatman Plc (Middlesex, UK), and others.

The present application describes a system for providing a prism-based refractometer in each well of a multi-well structure, such as a standard microplate. It can also be a single row well structure. Or it can be a two-dimensional well structure but made to a nonstandard geometry. It also provides gratings and waveguides in each well of a microplate. In one embodiment, prism elements are molded from a transparent polymer into the microplate bottom to form an integrated assay sensor unibody microplate. In another embodiment a layer of metal is integrated into these cell bottoms to provide SPR analysis. In another embodiment gratings and wave guides are integrated into separate cell bottoms for later attachment to microplates for optical biosensor measurements or intereferometric measurements. Images produced by the refractometer are filtered using a Discrete Cosine Transform (DCT) to remove high-frequency noise and improve accuracy.

An optical schematic of automatic prism-based refractometer 20, such as that disclosed in the '616 patent is shown in FIG. 1. Prism 20 is typically made of glass, usually a high-index flint glass with a refractive index between 1.7 and 1.8. Prism 20 has measurement surface 22 oriented upward so liquid samples can be placed on this measurement surface 22. Light source 24 is configured to approximate a point source or a line source with interrogation rays 26 fanned out through a range of angles. Fan of interrogation rays 26 enters prism 20 through entrance surface 28 at angles typically within about 20 degrees of normal. Interrogation rays 26 refract upon entering prism 20, bending toward entrance surface 28 normal as they transition from the low-index air into the high-index glass.

Fan of interrogation rays 26 propagates through prism 20 to measuring surface 22 where a sample (not shown) with a refractive index $n_{sample}$ has been placed in intimate contact with measuring surface 22 of prism 20 which has refractive index $n_{prism}$. Rays 30 at low angles of incidence where $\sin \theta < n_{sample}/n_{prism}$ exit through measuring surface 22. Ray 32, at the critical angle where $\sin \theta = n_{sample}/n_{prism}$ propagates along measurement surface 22. Rays incident upon measuring surface 22 at angles greater than the critical angle reflect from measuring surface 22 by total internal reflection (TIR) and exit prism 20 as exiting rays 34.

Exiting rays 34 form an illuminated area 36 on sensing surface 38 of detector 40, which may be a device, such as a charged-coupled device (CCD) or a CMOS imaging array. Such a detector 40 is characterized by two coordinate directions x and y, as shown in FIG. 1. A number of pixels in those directions define the x and y coordinates. With lower index samples, more rays are reflected from measuring surface 22, and illuminated area 36 on sensing surface 38 is larger. With higher index samples, fewer rays are reflected and illuminated area 36 is smaller due to an effective shift of edge 42 of illuminated area 36 in the y direction. Simple methods for processing of the electronic image generated by detector 40 to calculate a measurement have been described in the '616 and '576 patents.

Figure 2:
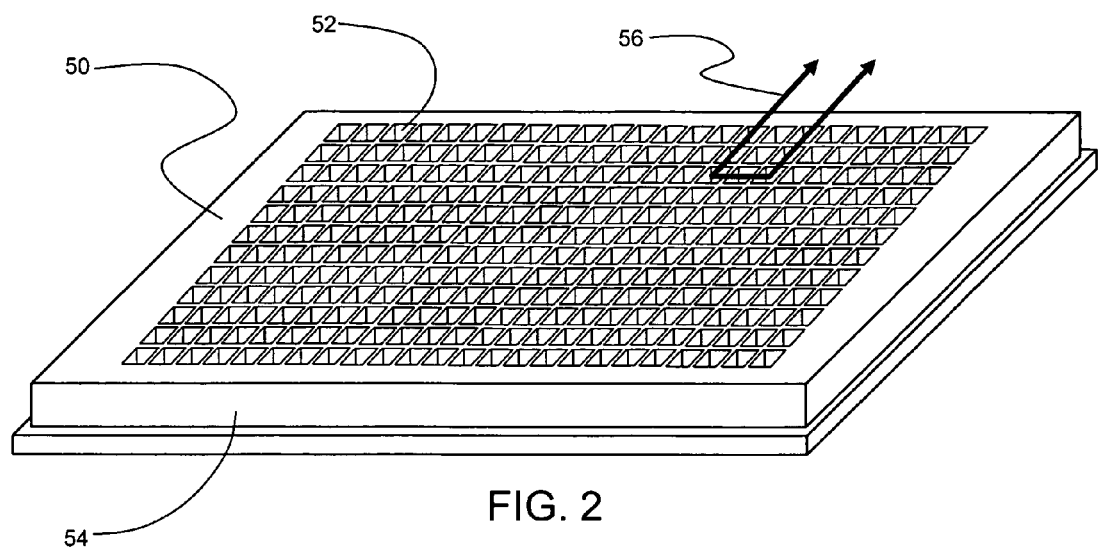
FIG. 2 is a three-dimensional view of a 384-well unibody microplate based on Society for Biomolecular Screening (SBS) standards illustrating one embodiment in which wells have a prism-shaped well bottom.

A 384-well microplate 50, in the form defined by the SBS microplage standards, is illustrated in FIG. 2. Microplate 50 consists of row and column array of wells 52 and surrounding skirt area 54 to support wells 52. In a 384-well plate, wells 52 are located on 4.5 mm centers. FIG. 2 shows an exemplary 384-well microplate 50, but microplates with 24, 96 and 1,536 wells are also commonly used in life science research and drug discovery. A microplate with any other number of wells can also be used. Samples and assay reagents can be placed in wells 52 for processing or measuring. Section line 56 in FIG. 2 shows an area in array of wells 52 from which detailed cross-sectional views are drawn. Molded microplates made of optically transparent polystyrene are available from many vendors, including Perkin Elmer (Boston, Mass.), Nalge Nunc International (Rochester, N.Y.), Corning Inc. Life Sciences (Acton, Mass.), Whatman Plc (Middlesex, UK), and others.

Figure 3:
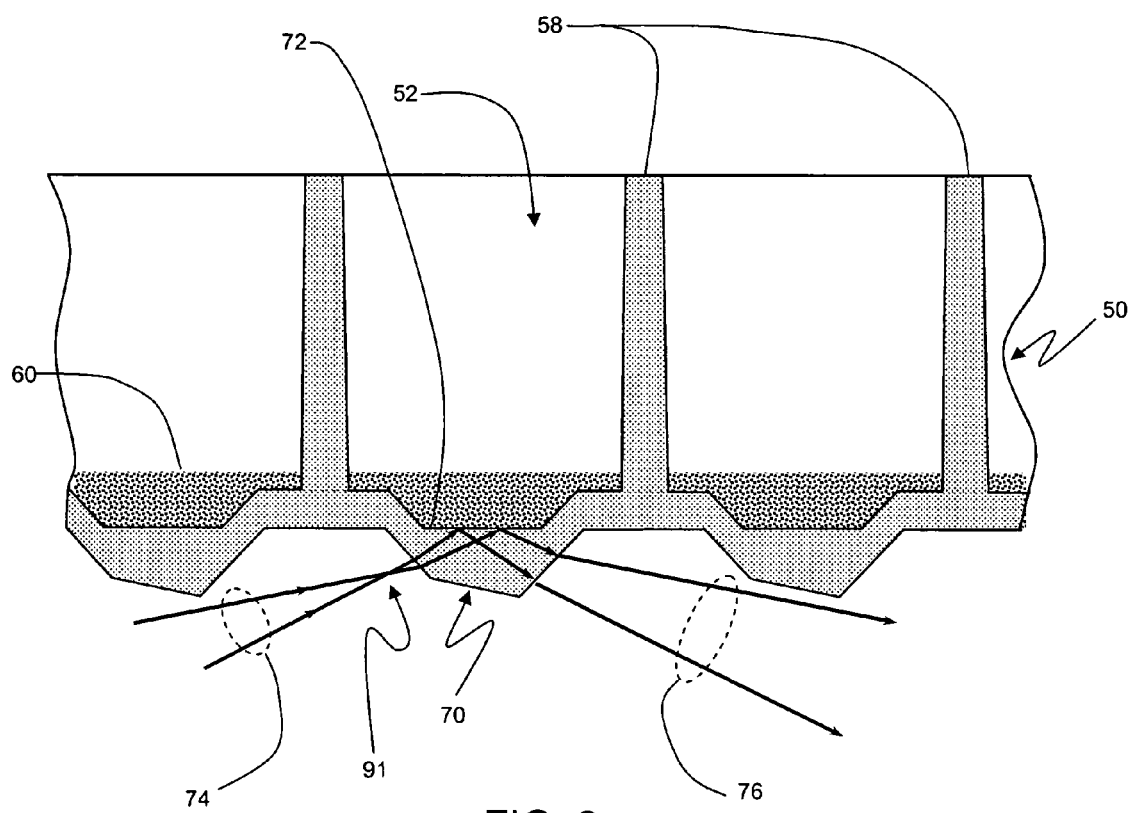
FIG. 3 is a cross sectional schematic illustrating one embodiment, showing an enlarged view of several wells of the unibody microplate illustrated in FIG. 2 showing the refractometer prism formed as the microplate well bottom, and the path of light through the prism.

A cross sectional view of a few microplate wells 52, is shown in FIG. 3. The operational details will be described for the central well shown in FIG. 3, but the same features and phenomena can be replicated in, for example, all of wells of unibody microplate 50. Wells 52 are spaced on 4.5 mm centers. There is a web of solid material forming walls 58 between wells 52. Walls 58 are about 1 mm thick, shown here with one-degree draft angles causing walls 58 to be tapered toward the top to facilitate molding. Sample 60 is shown in the bottom of wells 52.

Prism 70, in the form of an irregular and truncated trapezoid, is shown integrated into the bottom of each well 52 of unibody microplate 50, as shown in FIG. 3. Prism 70 has measuring surface 72 as its top surface, and this measuring surface 72 forms at least a portion of the bottom of each well 52. Prism 70 is configured to accommodate a fan of input interrogation light rays 74 that are directed upward at an angle to the bottom of microplate 50. These interrogation rays 74 refract upon entering prism 70 and propagate inside prism 70 to measuring surface 72. Subsets of interrogation rays 74 delimited by angle will either transmit through measuring surface 72 or reflect by TIR, depending on the refractive index of the sample on measuring surface 72. The subset of exiting rays 76 that reflected from measuring surface 72 exit prism 70 below microplate 50.

Figure 4:
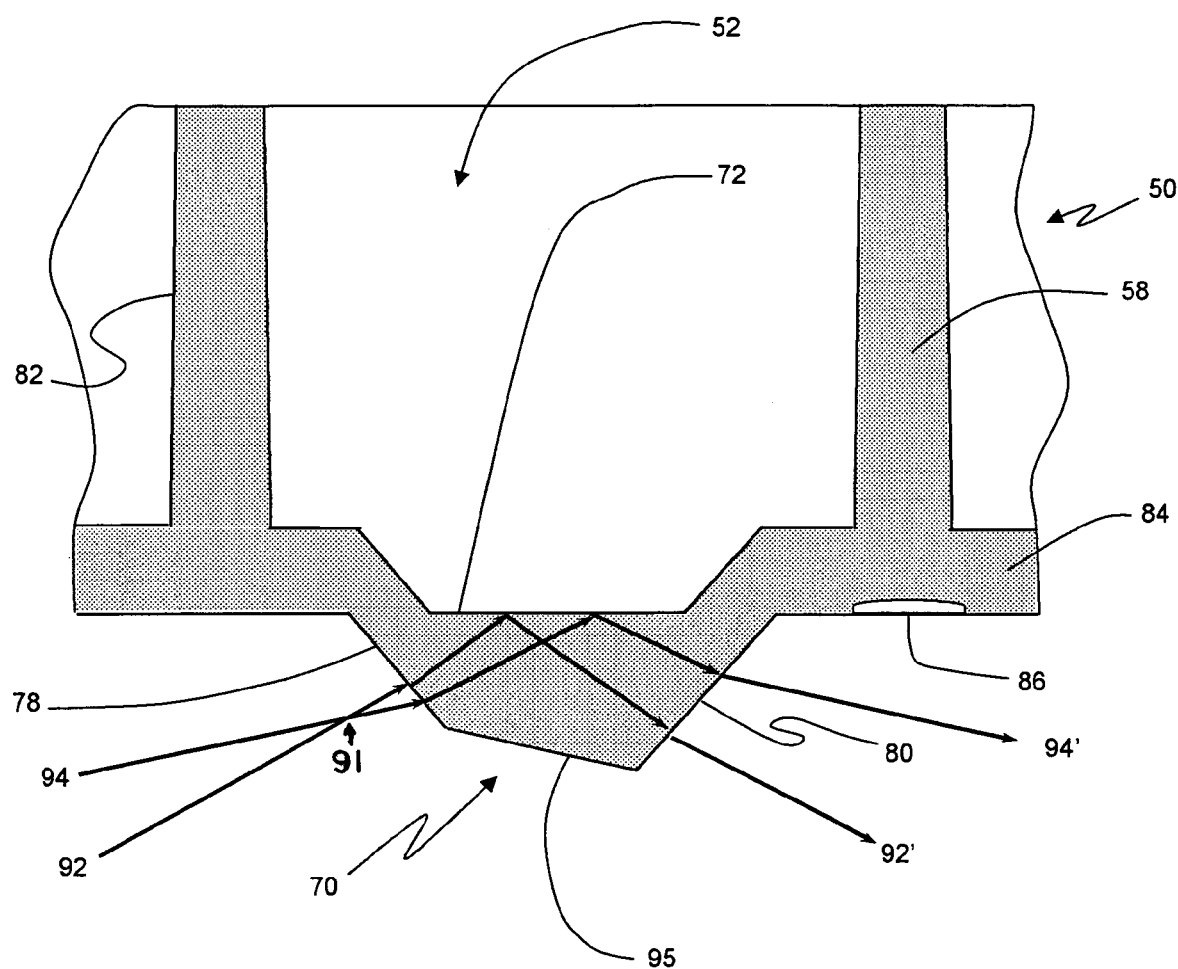
FIG. 4 is an enlarged cross sectional schematic of one well of the unibody microplate of FIGS. 2 and 3, showing the path of light through the prism.

An enlarged view of irregular trapezoid prism 70 integrated into the bottom of well 52 of microplate 50 is shown in FIG. 4. Irregular trapezoid prism 70 has three optical surfaces: entrance facet 78, measurement surface 72, and exit facet 80. Prism 70 is shown integrated into well 52 and well 52 in turn is integrated into a support structure, such as unibody microplate 50, which has an array of wells like well 52. The geometry of prism 70 has been designed in a manner consistent with obtaining high-quality results from the injection molding process normally used to form microplates. In this embodiment, unibody microplate 50 is molded from a transparent polymer such as polystyrene or polycarbonate. Prism 70 is integrated with bottom surface structure of unibody microplate 50, which in turn is integrated with webs 82 that form walls 58 that separate wells 52 from each other. Thickness or vertical dimension of prisms 70 varies along its length from about 1 mm to about 1.5 mm.

The geometry of prisms 70 with wells 52 and support structure shown in FIG. 4, illustrates their suitability for the injection molding process normally used for fabricating standard microplates without such prisms. Walls 58 between wells 52 are shown with a one degree draft angle to facilitate part ejection from that side of the mold during fabrication. The bottom or prism side of the mold exhibits large angle drafts, allowing the mold to pull directly away from the input facet 78 and output facet 80 while preserving their high quality optical surfaces. Prisms 70 themselves fulfill their optical functions while restricting their maximum thickness to about 1.5 times that of the nominal microplate thickness, which has a thickness dimension between about 1 and 2 mm. This facilitates cooling in the mold with minimal warping. Providing a high ratio of surface area to mass further facilitates the molding process. Finally, the junction of plate walls 58 to plate bottom 84, which may form sink mark 86 in plate bottom 84 upon polymer cooling and shrinking, is remote from the area of prism 70. This geometry allows ease of microplate manufacture while retaining maximum optical quality of the prism's optical facets. U.S. Pat. No. 6,790,388, incorporated herein by reference, describes the manufacture.

The prism geometry provided in this application differs significantly from prisms used in prior art analytical refractometers. Early analytical refractometer instruments used triangular high-index glass prisms 20, as shown in FIG. 1. While this geometry would superficially appear to be moldable in plastic, it does not accommodate closely-spaced wells 52 in unibody microplate 50. Point 90 of the triangle opposite measurement surface 22 interferes with paths of both interrogation rays 26 and measurement rays 34 on adjacent wells, when implemented in polymer materials with well spacing at the 9 and 4.5 mm standards used in 96- and 384-well microplates.

Cutting off prism tip 90 (FIG. 1) to provide fourth facet 95 makes prism 70 thinner and therefore easier to mold. It also allows detector 40 to be located closer to prism 70 without interfering with relative movement there between.

Figure 5A:
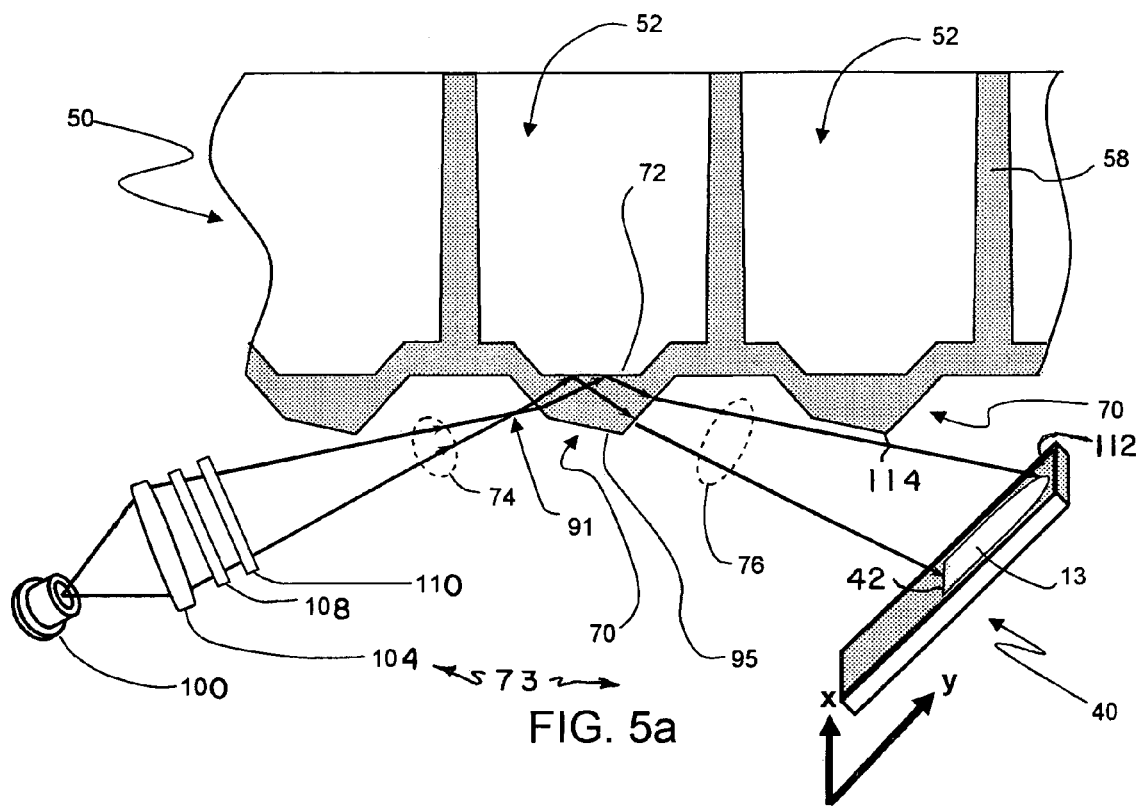
FIG. 5a is another cross sectional schematic of the unibody microplate of FIGS. 2–4 with a light source, beam shaping optics, filter, and a Charge Coupled Device (CCD) array detector.

Because beam 74 is fanning out from point source 91, output fan 92'–94' reflecting off measuring surface 72 and existing facet 80, notwithstanding the transmitted portion output fan 92'–94' could be wider than input fan 92–94 entering input facet 78. So it is desirable that the output facet 80 be larger than input facet 78, which makes prism 70 an irregular trapezoid having a sloping fourth facet 95, as shown in FIGS. 3, 4, 5*a*. Also it is desirable to have a focal point 91 that provides the input fan 92–94 as close to input facet 78 as possible to keep input fan 92–94 as small as possible so the area of optical quality prism can be smaller and so output fan 92'–94' does not get wider than facet 80, producing undesired results.

Current instruments, such as the Leica Microsystems units described in the '809 patent and the '576 patent references, use 4-facet glass prisms in the form of a regular trapezoid with a common input and output facet opposite the measuring surface. In these prior art prisms the nonparallel side facets are used to provide TIR beam steering of all interrogation rays and reflected measurement rays. The beam steering TIR approach with two internal reflections works particularly with the high-index glass prisms but become increasingly difficult as index decreases, such as low-index polymer prisms (e.g. polystyrene at n=1.59).

Ray paths 92–92' and 94–94' illustrate boundary conditions in one embodiment. The angles shown assume a polystyrene polymer prism with a refractive index of 1.59. Interrogation ray 92 and its downstream refracted and reflected ray 92' follows the path of the first ray to be TIR reflected past the critical angle with a sample index of 1.33, the index of water on measuring surface 72. It is important for an assay measurement apparatus or system to accommodate water at the low-index end of the measurement range because aqueous buffers in widespread use, such as PBS or SSC, have refractive indices only slightly higher than water. Accommodating measurements of these low refractive indices of assay products allows the apparatus or system to obtain an in-range measurement even when assay results are completely negative.

Interrogation ray 94 and its downstream refracted and reflected ray 94' follow the path for the first ray to be TIR reflected past the critical angle when the refractive index of the sample is 1.45. It is advantageous for the upper bound of the measurement range of such a device or system to be in excess of about 1.42 as this is the approximate index of bulk proteins. The ray traces shown here were provided in a computer simulation using a plastic prism and a plastic well, and demonstrate that an integrated refractometer prism with sufficient range to be of great utility in biological assays can be fabricated into a microplate well.

Figure 5B:
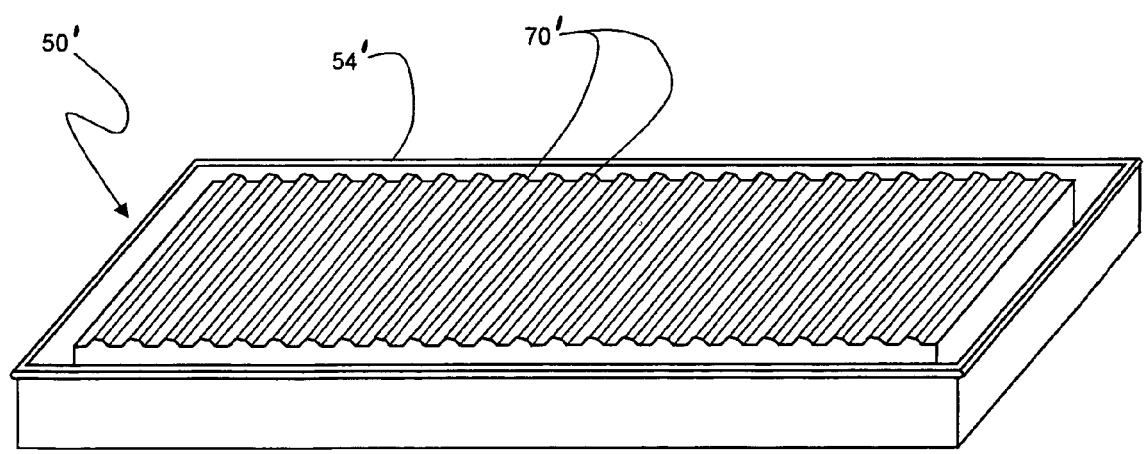
FIG. 5b is a three-dimensional bottom view of a unibody microplate having prisms that extend across columns of wells.

Prisms 70' may be molded as a monolithic structure that spans an entire row or column of wells 52 in unibody microplate 50', as shown in the bottom view of FIG. 5*b*. Microplate 50' has skirt area 54'. Alternatively, prisms 70 may be molded as discrete prisms, one for each well 52, as shown in cross section in FIGS. 3, 4, 5*a*. Monolithic multi-well prisms 70' shown in FIG. 5*b* include a simpler mold design and fabrication and produce a more mechanically rigid molded part. On the other hand separate, discrete prisms with gaps between them have a higher surface area to mass ratio and may freeze in the mold with less distortion. The choice of configuration is dependent upon the specifics of the mold design, molding material and molding process.

Microplate 50 is used along with reading instrument 73 for determining the index of refraction of samples in wells 52 is illustrated in FIG. 5*a*. Interrogation rays 74 and exiting rays 76 are shown at the angles representing measurements of samples on measurement surface 72 having indices of refraction of 1.33 and 1.42 respectively with prism 70 having an index of refraction of 1.59 (as in the example above). The geometry of prism 70, microplate 50, and other system components are specifically designed such that all components can be located without rays directed to or exiting one prism 70 being occluded by a prism 70 on adjacent wells 52.

Light source 100 produces light for interrogation rays 92, 94. Light source 100 may be, for example, a laser, a superluminescent diode (SLD), an LED, or a light bulb. SLDs and LEDs both have high brightness and high electrical efficiency. Standard analytical refractometers use yellow light sources with wavelengths around 589 nm because the published reference indices of refraction of many substances are determined at that wavelength. In using the present system for determining sample index of refraction during an assay, it is not important to measure absolute indices that can be compared with published data; rather the goal may be to quantify changes in properties of the sample due to the assay. An assay is a procedure to either measure the presence of a material or to measure how much of the material is in the sample, either its concentration or its quantity in a known volume. An assay frequently involves a measurement of a liquid biologically derived material. In the assay, one is looking for a constituent. However, few assays measure concentration directly. Most produce a signal that is calibrated to concentration in a calibration step. An investigator may, for example, make a standard curve of concentration v. signal. An investigator may also make a standard curve of amount v. signal in a standard volume. Calibration is accomplished by performing an assay with samples having a known concentration of the analyte. The investigator then interpolates between those known concentration points to provide a curve of concentration v. signal. Then, when an unknown sample is measured, the measured signal is compared with that curve to determine concentration of the analyte in the unknown sample. Thus, one does not need to ever calculate the index. One can go directly to concentration or amount in a known volume from the measurement signal.

Thus, a standardized reference wavelength light source, such as a yellow bulb, can be used, a nonstandard reference wavelength, such as a laser, can also be used.

Light from source 100 is focused by beam shaping optics 104, as shown in FIG. 5a. Beam shaping optics 104 produce interrogation rays 74 having a range of angles for obtaining the desired range of refractive index measurements. In FIG. 5a, interrogation rays 74 are shown converging to focus 91 just before prism 70. This focus 91 is a virtual point source from which fan of interrogation rays 74 can be viewed to originate. This configuration allows light source 100 and beam shaping optics 104 to be located further away from microplate 50. It also allows freedom of movment for microplate 50. Thus, a single set of light source 100 and detector 40 can be moved with respect to microplate 50 to measure any well in microplate 50.

Beam shaping optics 104 may be a conventional spherical lens. It can also be a cylinder lens or other anamorphic lens, having different properties in different directions. A cylinder lends creates a line focus at 91 so that interrogation rays 74 have the converging-diverging angles shown in the plane of FIG. 5a drawing, but are substantially collimated or parallel along the x direction. In this arrangement, the measurement of index of the material on measuring surface 72 is taken on a line across entire measuring surface 72 of well 52 in the x direction, rather than on a small point-like area on measuring surface 72. This reduces sensitivity to point defects in the optical path and helps to average out inhomogeneities or artifacts in the assay material on measuring surface 72 or in the optical path.

Wavelength filtering optics 108 may be incorporated into the light path of interrogation rays 74, depending on light source 100 and degree of accuracy required in index of refraction measurements. All materials, including the prism material, have chromatic dispersion or refractive indices that vary slightly with wavelength. Limiting interrogation rays 74 to a narrow band of wavelengths, say 10 or 20 nm, can reduce the effect of dispersion. If light source 100 is inherently monochromatic, such as a laser, wavelength filtering optics 108 would not be needed. With a coherent laser source, however, a diffuser element in the position of wavelength filtering optics 108 can reduce some of the image noise caused by laser speckle.

Polarization optics 110 may also be incorporated into the path of interrogation rays 74 depending on inherent polarization properties of light source 100. The interrogation rays 74 should be linearly polarized because the two different polarization states (TE and TM) have different critical angles and different angle vs. reflection behaviors near the critical angle, as described by the Fresnel reflection equations. Interrogation rays that includes both polarizations would produce output rays with two superimposed reflection patterns that would be difficult to interpret. In some embodiments, polarization is provided before light reaches prism 70 and before it reaches sample in contact with prism 70. Polarization is better provided in more parallel light, and thus polarization optics are provided closer to light source 100.

In analytical refractometers, the TE polarization is used most frequently because it has the sharpest transition between transmission and TIR. Either polarization may be used in a refractometer assay device. It may even be advantageous to configure the instrument to make sequential measurements with the two polarizations, as the evanescent wave of the TM beam protrudes further from the measurement surface than that of the TE beam. This technique has been used to help distinguish surface binding assay phenomena from bulk index changes in the assay media in waveguide-based biosensors, as described in the '793 patent.

Exiting rays 76 reflecting from measurement surface 72 by total internal reflection are all angled downward, as shown in FIG. 5a. Detector 40 is placed far enough away from microplate 50 that top 112 of detector 40 is below bottom surface 114 of microplate 50, allowing freedom of movement of microplate 50 with respect to detector 40 for detecting exiting rays 76 from other prisms 70 and other wells 52 of microplate 50. The arrangement is also specifically designed such that horizontal translation of microplate 50 is not blocked by mechanical interference between any prism 70 of microplate 50 and an optical component, such as those shown in FIG. 5a.

An embodiment of an apparatus capable of measuring refractive index changes from microplate 50 using either prism refractometry, as shown in FIG. 5a, or grating-waveguide interferometry as assay measurement modalities is shown in FIG. 6.

In this arrangement two sets of coexisting optical components are provided. The refractometery optical components described herein above for use with microplate 50 of FIG. 5a are shown in FIG. 6 as light source and interrogation optics 120 and refractometry image sensor detector 122. A reading instrument 73' including optical elements for making interferometric measurements 124 and 126 are all placed in space 128 between interrogation optics 120 and refractometry image sensor detector 122. Removable waveguide-interferometry microplate 128 is configured with gratings 130, 132 and planar waveguide structure 134 in each bottom surface 136 of well 138 instead of refractometer prisms 70 of FIG. 5a.

Bottom surface 136 of each well 138 in waveguide-interferometry microplate 128 has input grating 130 and output grading 132. Grating 130, 132 allow interrogation light rays 140a, 140b to enter waveguide structure 134 and allow exiting rays 142a 142b to exit bottom surface 136 at an angle determined by the dimensions of gratings 130, 132 and the wavelength of interrogation rays 140a, 140b. Gratings 130, 132 steer beams, changing their direction. They are particularly good for providing a wide beam into a narrow wave guide because they can turn each parallel ray 140*a*, 140*b* through the same angle. So the gratings 130, 132 have the right spacing, they can be used to steer beam 140*a*, 140*b* to couple into waveguide structure 134.

In FIG. 6 both sets of rays 140*a*, 140*b*, 142*a*, 142*b* are shown at about 15 degrees from normal 144 of bottom surface 136 of microplate 128. Interrogation beams 140*a*, 140*b* impinge on transparent bottom surface 136 of microplate 128 and refract slightly toward normal 144. Input grating 130 couples interrogation beams 140*a*, 140*b* into high-index thin-film planar waveguide layer 146 on bottom surface 136 of microplate 128. Two separate waveguides can be provided or one waveguide wide enough to provide space for two beams traveling separately can be provided. Such waveguides are often made of tantalum pentoxide or titanium dioxide layers a few tens of nanometers thick, deposited on bottom surfaces 136 of microplate 128, most often by vacuum sputtering.

Each of the two interrogation beams 140*a*, 140*b* propagates in waveguide layer 146, as shown by arrows 148. One of these beams (the measurement beam) is exposed to the sample or assay (not shown) in well 138, while the other (the reference beam) is masked from contact with the sample. The masking can be done in a variety of ways, such as placing inter-well wall 160 over the reference beam, coating an additional low-index transparent material on top of the reference path, or by directing the reference beam to propagate along the bottom of an adjacent separate reference well (not shown) having no assay material.

Thus, one path is not exposed to the analyte material while the other path is exposed to the analyte material. The paths can be in adjacent wells, with assay conditions in one well and reference conditions in the other. Alternatively, one can mask a separate reference path while leaving a measurement path exposed in one well. For example, an isolating layer may be provided covering half of the bottom of each well. In another alternative, reference beam 140*b* could travel in a wave guide located under wall 160. A glued together or adhesively connected structure makes these alternatives possible. One can measure a change in index because the index of binding material right next to bottom surface 136 of well 138 is affected by any binding it experiences, and that change in index can be measured. Alternatively, if antibodies are immobilized on only one half of bottom surface 136 then there will only be an interaction on that half, and difference in index between halves can be used to determine presence of a binding material and the magnitude of binding. Antibodies can be printed on half of bottom surface 136 using an ink jet printer like device. Alternatively, one can tip microplate 50, 128 at a 45 degree angle so that a liquid only covers that one side of bottom surface 136.

Two beams 140*a*, 140*b* propagate through planar waveguide 134 until they reach output grating coupler 132, which directs two beams 140*a*, 140*b* out of waveguide 134, through transparent plate bottom 136, and into the air below bottom plate 136 as exiting beams 142*a*, 142*b*. Two exiting beams 142*a*, 142*b* are allowed to interfere through pair of slits 162 to form fringe pattern or interferogram 164. Alternatively, slits 162 can be omitted as described by Freeman, who uses coherent light and two physically separated waveguides, and therefore does not need slits. The shape and location of fringe pattern 164 is detected and transformed into an electronic image by imaging array detector 166, such as a CCD array.

On the input or interrogation side, light source 168 produces light 170 which is made into a beam by optional beam-forming optics 172. Light source 168 may be coherent, for example, a laser, as described by Hartman and Freeman, or it may be incoherent such as a superluminescent diode (SLD), as described by Brandenburg. If light source 168 is a diode laser or an SLD, beam forming optics such as a collimating lens are required to collect the light into approximately collimated or parallel beam 174. Other light sources, such as HeNe lasers, produce collimated beams intrinsically. The beam is split into two portions, reference and measurement, by beam dividing element 176. This can be a pair of slits or apertures as shown, another beamsplitter arrangement, such as a partially reflective beam splitter, or a grating.

Refractometry source optics 120 and detector 122 inherently need to operate at fairly large incidence angles with respect to bottom surface 136 of microplate 128, as shown in FIG. 6. The nominal central incidence angle for light from refractometry source optics 120 is 67 degrees in the example shown in FIG. 6. That is, the direction of the central ray of the fan of rays from source optics 120, which defines the direction of the entire fan of beams from source optics 120 has an angle of incidence of 67 degrees in FIG. 6. This large angle is used because the TIR critical angle to air in polystyrene and other transparent polymers used to mold microplates is within a few degrees of this angle. Gratings for coupling light into and out of well-bottom waveguides, in contrast, work better at considerably smaller incidence angles. In some embodiments, they allow light in and out of flat-bottom plates at near-normal angles in order to keep Fresnel reflection from parasitically consuming the majority of the incident light. The scheme illustrated in FIG. 6 of a combined measurement instrument that can provide data for either prism refractometry or waveguide interferometry is enabled by the recognition of the two modalities' differing angle requirements, allowing optics for the grating scheme to fit between optics for the prism scheme.

Such a combined instrument offers significant savings in cost and laboratory space over the two separate instruments that ordinarily would be required to read both the inexpensive refractometer well structures and the more sensitive but more expensive interferometer well structures. Both modalities use similar light sources and can be configured to use identical light sources, such as an SLD. Both use area imaging detectors and can be configured to use similar or even identical detectors. In such a configuration all of the other components of the instrument such as the light source control electronics, the image acquisition electronics, the image processing electronics, the well-addressing mechanism, the power supply, the system controller, and the instrument structure and enclosure can be common.

Figure 9A:
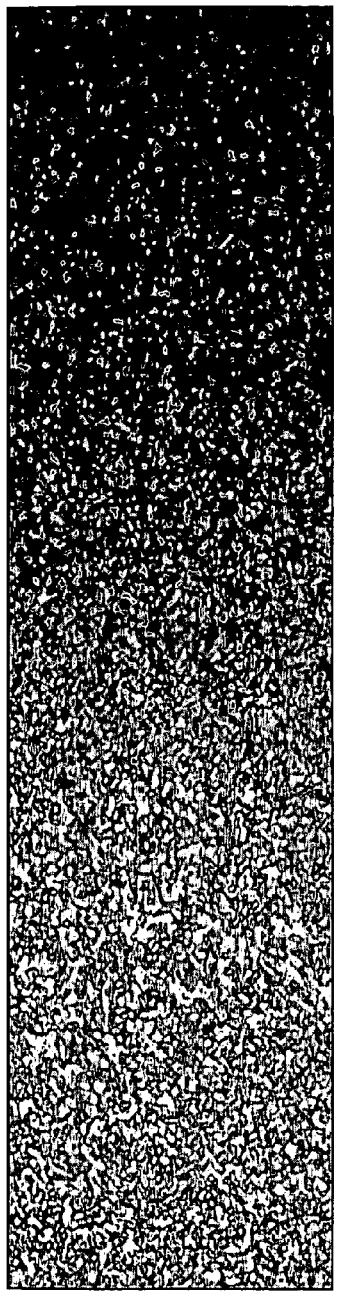
FIGS. 9a–9c show three prism refractometer images generated by coherent laser light source with a diffuser in the interrogation light path.
Figure 9B:
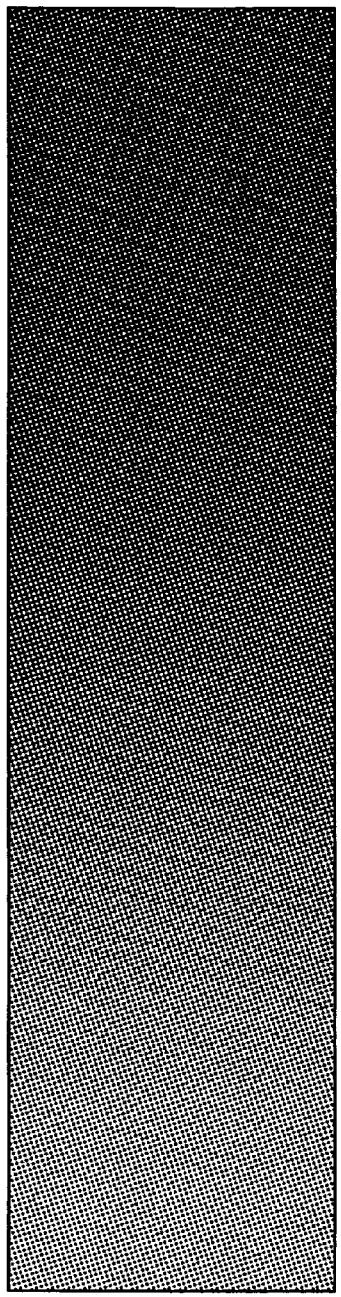
Figure 9C:
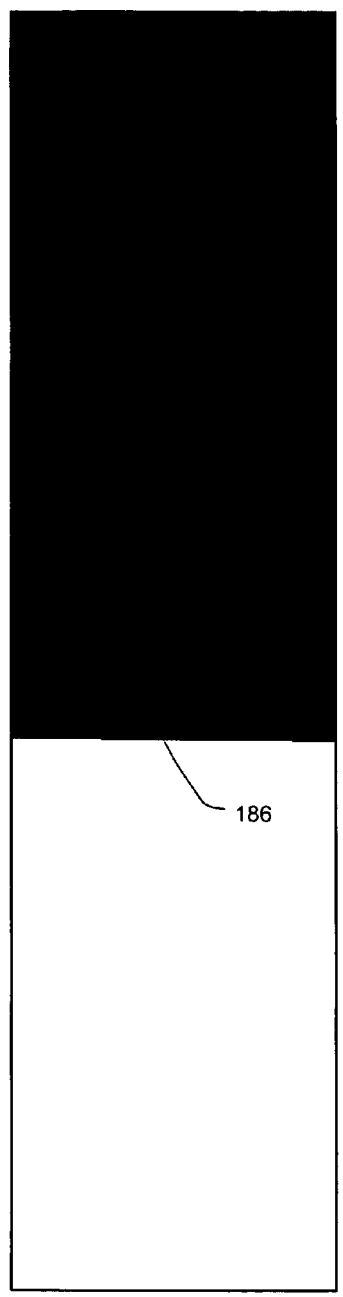

FIGS. 9*a*–9*c* show three versions of prism refractometer images created by the apparatus in FIG. 5*a* by glass prism 70 (Melles Griot 01 PRP 009/078), a sample (not shown), and reading instrument 73, including laser light source 100 and detector 40. Reading instrument 73 also includes positioning mechanics (not shown) to position microplate 50 and prism 70 with respect to reading instrument 73 so light from light source comes to focus 91 close to facet 78 and so reflected light shines on detector 40. Light source 100 used for these images was a coherent helium-neon (HeNe) laser, and optics 104, 108, 110 included a cylindrical lens with an effective focal length of 10 mm (Thorlabs LJ1878L1-A). The sample placed on prism measuring surface 72 was a solution of 9.5% glycerol in water. Imaging detector 40 was a ½ inch format CMOS sensor (Luminera Corporation, LUI05M), with 1,280×1,024 pixels, each 5.2 microns square. The images were acquired into a PC (not shown) connected to detector 40 running MATLAB image processing software V6.5.1.

Positioning mechanics (not shown) also provide relative movement between reading instrument 73, 73' and microplate 50, 128, so measurements can be taken of samples in successive wells 52, 138 of microplate 50, 128.

Figure 7:
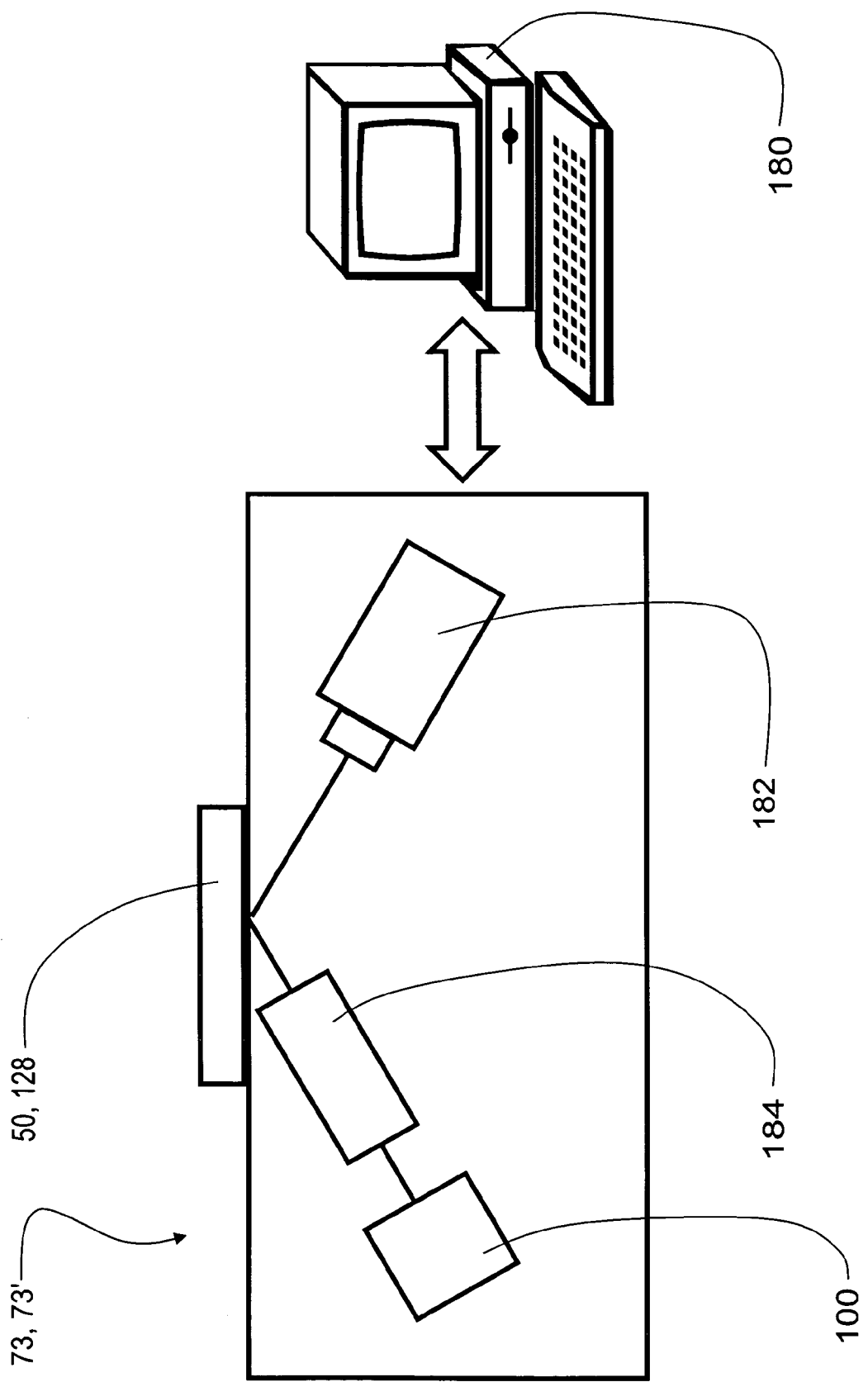
FIG. 7 is a block diagram showing components of one embodiment.
Figure 8:
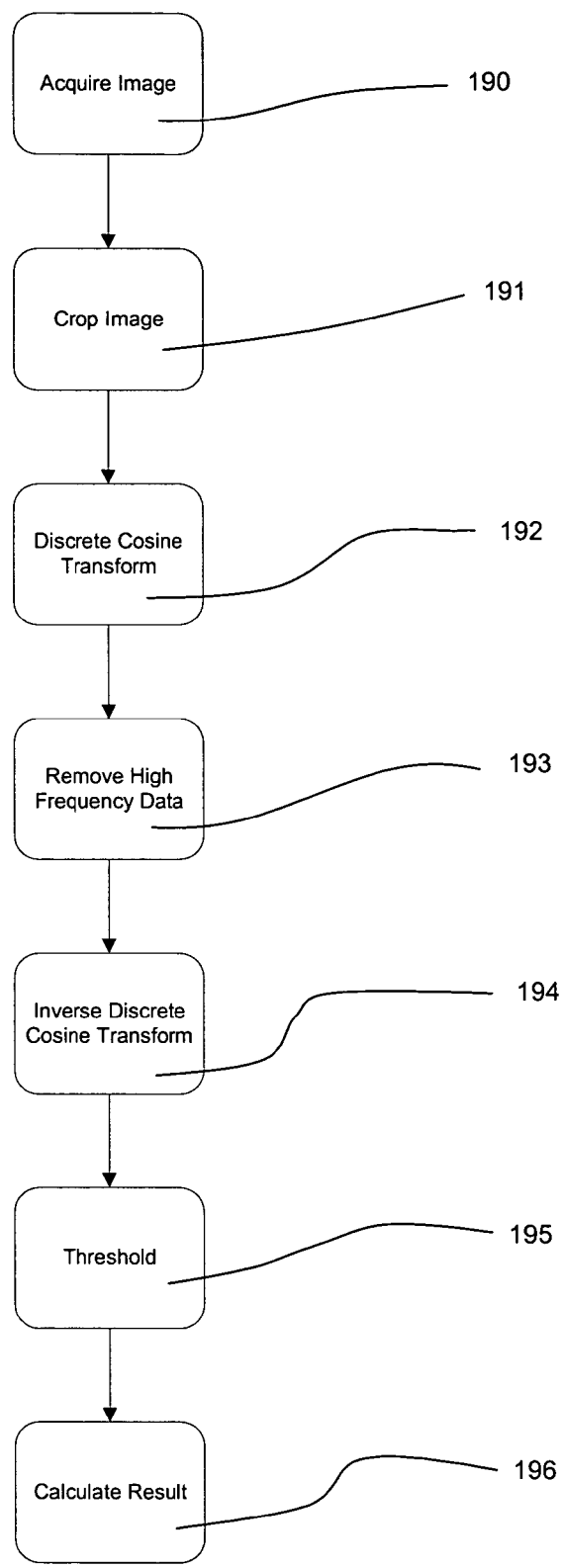
FIG. 8 is a flow chart of the process of one embodiment.

The raw image is acquired by computer 180 from standard CMOS or CCD camera 182, which is stationary and fixed to optical apparatus 184, as shown in FIGS. 5a, 6, and 7 and in box 190 of the flow chart of FIG. 8. The acquired image is then cropped or truncated to 250 pixels in width to eliminate edge effects, as shown in FIG. 9A and in box 191. The amount of cropping can be adjusted to improved processing speed or signal to noise performance. Smaller images provide faster results but with potentially a lower signal to noise ratio. The expected light-to-dark transition is visible from bottom to top of FIG. 9a but there is a great deal of high-frequency noise limiting the ability to resolve a transition, and from that transition, the refractive index of the sample. Noise in the raw image is caused by laser speckle and by interference, tiny defects in the prism or other optics, dust, etc.

Prism refractometry with light sources, such as lasers, produces a noisy image, like that of FIG. 9a. Coherent sources, such as lasers, are the noisiest because laser light has been through many partial internal reflections in the optics through which the light is propagated. During these many reflections the light has the chance to interfere with itself. Such coherent light may also travel along different paths in the laser and from the laser, and beams traveling along the different paths may also interfere when their paths cross. Thus, laser light is an interferogram having many high frequency components provided by the self interference, and this is the reason for the speckle appearance of laser light.

Precision in detecting the critical angle is limited by size of the light source. If the light comes from a spatially dispersed source, such as a light bulb, light rays would be coming from all of the different point sources that make up the dispersed source, such as the filament of the bulb, and each would provide a different edge than the others, resulting in an image that has no sharp edge. Therefore, sensitivity to change in index of the material in contact with the measuring surface of the prism would be reduced. To get a sharp edge a point source as origin of the fan of beams is preferable. Providing a point source is very easily accomplished with a laser and very difficultly with an LED, which is an area emitter, or a bulb, which is a line emitter. Of course an LED or bulb eliminates the speckle noise problem, and other techniques are available to provide good point sources, so LEDs and bulbs have been successfully used in many analytical refractometers. But those instruments have not been sensitive enough to look for as small a change in index as may be produced by a biological reaction.

Thus, the present teachings overcome the speckle limit of lasers and use the special advantage of lasers for prism refractometry that their light can be focused very precisely. Accordingly, the light fanning out from such a small diffraction limited point source has the potential to provide a sharp fundamental straight line edge 186 (FIG. 9c) on the detector, providing greater sensitivity for the prism refractometer to detect the critical angle—the angle where transmission stops and reflection starts—and to be sensitive to small changes in index of refraction.

The noise reduction includes Discrete Cosine Transform (DCT) to transform the image of FIG. 9a to frequency domain, as shown in FIG. 9b and in box 192. One can use DCT to select a band of frequencies in an image to retain or to remove. In the present application only one cycle of information, the fundamental frequency is desired, as the image is expected to be a line separating a dark region from an illuminated region. The spacial frequency of the desired image is one cycle across the whole detector. DCT and other similar processing schemes allow attenuating or removing other higher spatial frequencies. When high frequency components are set to zero and removed and the fundamental frequency is retained, the edge is revealed, as shown in box 193. FIG. 9c shows the image after applying this filtering to remove high frequency components and then applying an inverse DCT transformation, as shown in box 194, and thresholding in box 195 to provide the image representation and to provide a sharp transition in the image. The inverse DCT transformation transforms the data back to an image, only now with the high frequency data removed by the filtering. One goal of the transformations and filtering is to obtain an image with a single clear continuous boundary between light and dark regions. In thresholding, the image is reduced to a binary representation based on applying a threshold intensity value, as shown in box 195. (Note: FIGS. 9b, 10b, 11a, and 11b are rendered in hailstone dots in this patent application in order to show image fidelity within the constraint of the binary .tif image format required for patent application electronic filing. As actually created, the images have no half-tone dot pattern).

The resulting image in FIG. 9c shows almost none of the high-frequency noise or artifacts; instead, the expected monotonic light-to-dark transition is clearly visible. Thus, the DCT provides the ability to take advantage of lasers to substantially improve resolution for prism refractometry. FIG. 9c also shows the DCT transformed image with a threshold applied to create a binary image with one white zone and one black zone. The location of the light-to-dark transition, and hence the refractive index, can be quantified using this thresholded image. In this embodiment, the simple ratio of the total number of black pixels to the total pixels was used, as shown in box 196, although other processing schemes may be employed. The ratio indicates the position of the light-dark transition on detector 40, 122 or camera 182 with a scale from zero to one. Changes in this result correlate with changes in the index of refraction of the sample material in well 52, 138.

The ratio of black to total pixels provides the reading as a single digital number. To get one number includes deciding where that line falls on a discrete scale. The decision as to what threshold to use to distinguish black from white areas can affect the result. Thresholding involves classifying intensities into just two bins, dark and light. Everything below the selected threshold level is dark, while everything above it is light. The ratio is found by dividing the total number of pixels below the threshold level by the total number of pixels, giving the fraction below the threshold intensity. This approach gives the analysis by area instead of by line. It accommodates the possibility that the line may be wavy or slanted. By taking the area, one removes the shape of the line from the analysis. If there is a shift in index then the area will shift and one does not have to worry about the details of the transition line. Counting the fraction of pixels that are white or black provides an excellent method of detecting a change in index. A change in the ratio will track a change in index of refraction as the binding reaction proceeds after a chemical or reagent is added to the microplate well.

While the original image shown in FIG. 9a does not have a sharp transition from black to white, by filtering out high frequency artifacts one gets much closer to a binary image with just two intensities. Thresholding further gives contrast to the image. As long as one keeps the same threshold value before and after the sample one sees the shift in index. One can get a good result with a fairly wide range of choices of the threshold.

In the present application DCT or its variants (e.g. Discrete Fourier Transform, Modified Discrete Cosine Transform, etc.) are used to process prism refractometer images to remove high-spatial-frequency noise therefrom. The binary thresholding processing scheme is then applied to DCT transformed images to calculate the position of the light-dark transition line and hence the refractive index of the sample.

In the present application of DCT the image may, for example, be black on top and white on the bottom with a line marking the transition region there between. Investigators may adjust parameters of the equipment and the DCT analysis to select how much detail they would leave along the line separating dark and light areas as well as perpendicular to that line. Providing more pixels from left to right gives better noise immunity since there are more data points, and one can average over a large number of pixels to improve the signal to noise ratio. Perpendicular to the line one can choose the amount of filtering to use to determine how sharp the line is. The present inventors found that they may get slope to the line if there is an alignment issue with the setup, for example, if the sample is not orthogonal to the detector. It is possible to use this feature to perform an optical alignment.

Figure 10A:
FIGS. 10a–10c show three prism refractometer images generated by coherent laser light source with no diffuser.
Figure 10B:
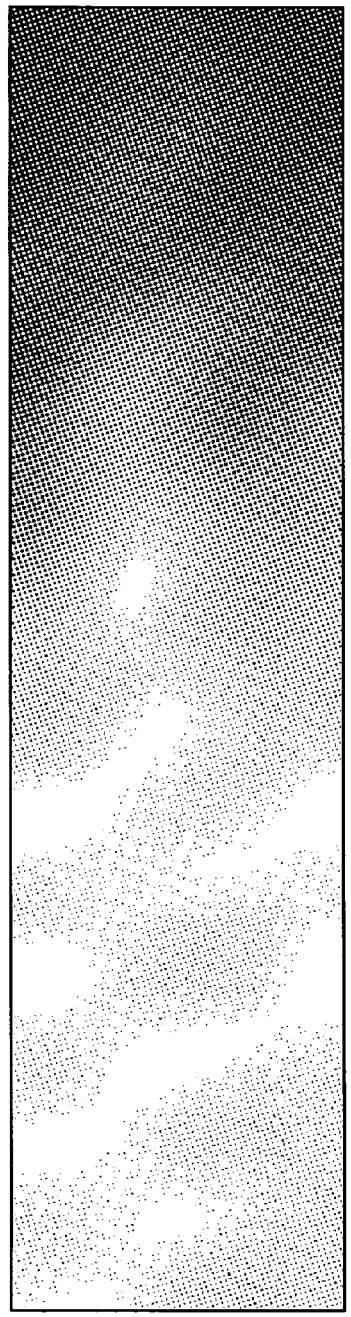
Figure 10C:
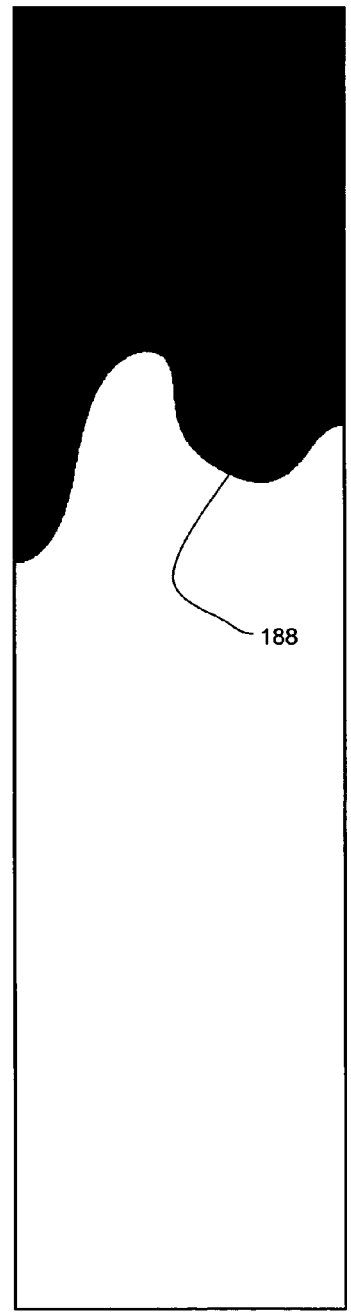

FIGS. 10a–10c shows the same sequence of three images as FIGS. 9a–9c, except using light generated by the coherent laser without a diffuser. In the raw image in FIG. 10a is a pattern of noise, primarily speckle and overlapping interferograms. In this case the sample on the prism was water. FIG. 10b again shows the image of FIG. 10a after performing a DCT, high frequency component removal, and inverse DCT. FIG. 10c shows the thresholded binary image, again with a line between light and dark regions but this time the line 188 is wavy.

The image processing for FIGS. 9c and 10c was performed using the MATLAB (The Mathworks, Inc., Natick Mass.) functions "imcrop" to crop the image width to dimensions x=256 while preserving the original y=1,280, "dct2" to produce a two-dimensional DCT of the raw image, "idct2" to perform the inverse transform, "im2bw" to perform the thresholding. The DCT and thresholding algorithms are among the add on modules in the MATLAB image processing toolbox. The DCT and thresholding algorithms can be implemented in a variety of image-processing platforms such as a dedicated processor in an instrument or in a workstation computer controlling in instrument.

Figure 11A:
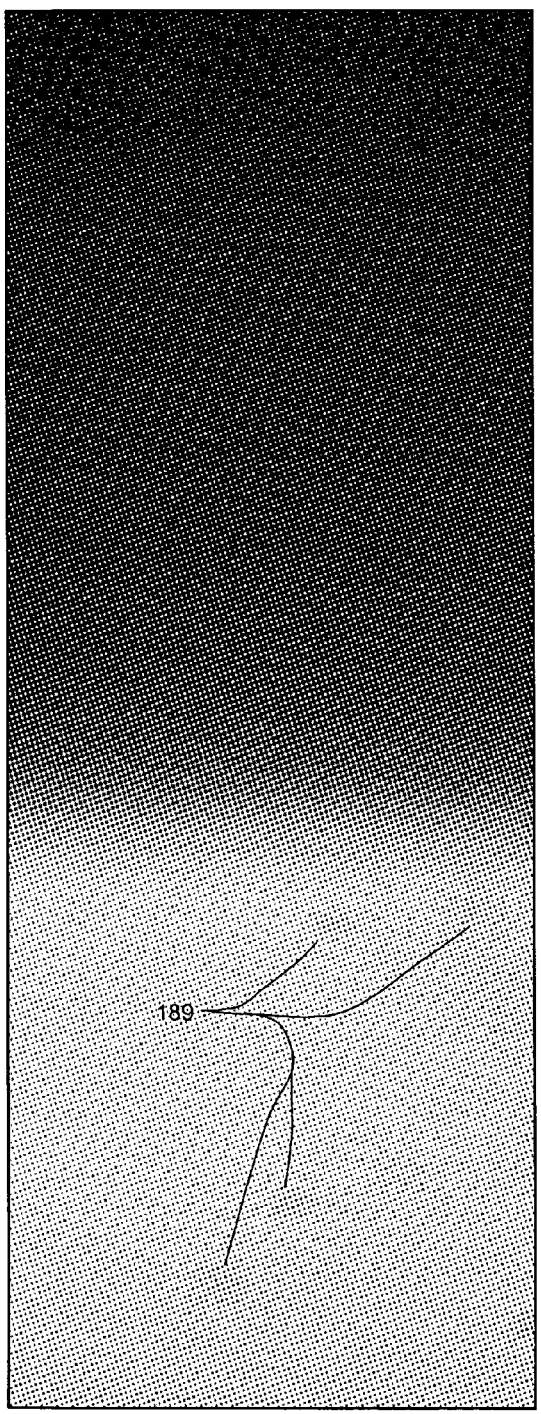
FIGS. 11a–11b show two prism refractometer images generated by non-coherent LED light with a collimating lens and no diffuser.
Figure 11B:
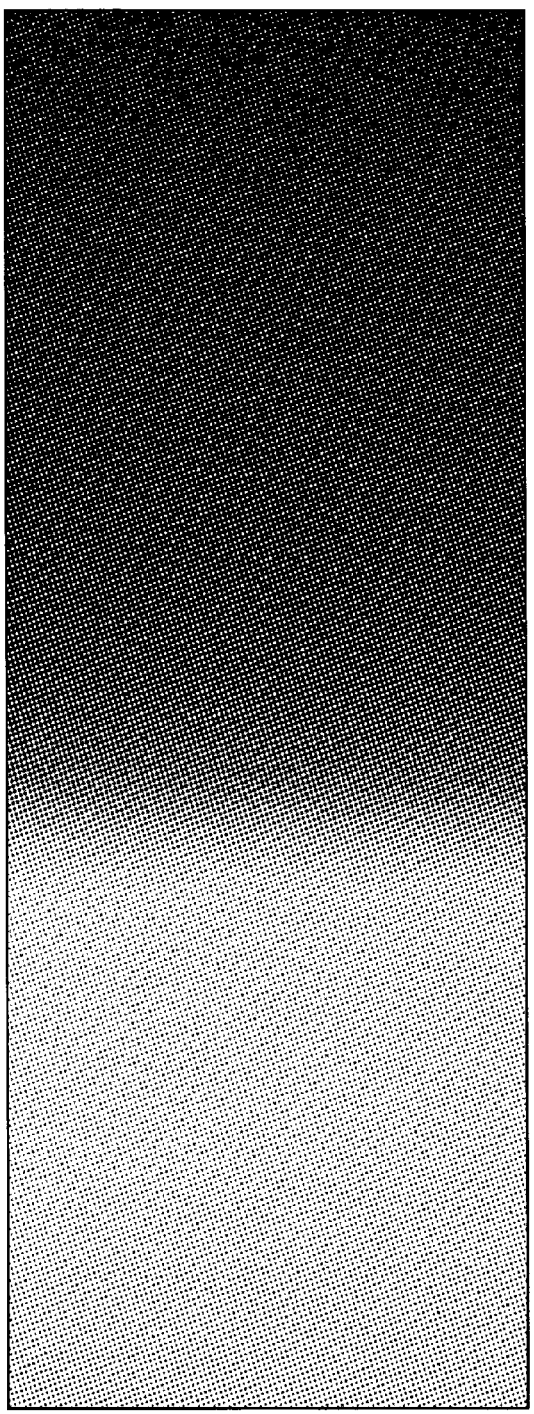

FIGS. 11a–11b show the DCT process applied to prism refractometer images generated with an LED light source rather than a laser. In this case, the LED produced light at a nominal 627 nm (Lumileds Lighting LXHL-PD01). The beam forming optics included a collimating lens (Melles Griot Achromat 06 LAI 007/076) with a 40 mm effective focal length between the LED and the cylindrical lens. The sample in this case was 5% glycerol in water. The LED images have less high-frequency noise than the laser images but still exhibit artifacts that pose problems in quantitation. In FIG. 11a, several dark round artifacts 189 are apparent in the light area of the image. FIG. 11b shows the image after performing the DCT, truncating the high frequency components, and performing the inverse DCT. The artifacts are removed. The reverse DCT converts the frequency domain data back to an image of a two dimensional array of pixels each with an intensity an image but with the high frequency portion of the data removed. The LED light source provides a wider spectrum of light and a less well defined transition but since there is no speckle less filtering is needed. In some cases a laser with the DCT filtering provides higher resolution; in others the LED may provide higher resolution.

Different microplates 50, and even different types of the microplates 50, 128, can be installed and measured in the same reading instrument 73, 73' of FIGS. 5a and 6. Microplates 50, 128 may be disposable as well as interchangeable. Prisms for microplate 50 may be made of glass, polymer, or another transparent material at the desired interrogation wavelength, which may be in the visible or near infrared range, mostly determined by availability of light sources and detectors and transparent prisms in the desired wavelength range.

Glass prisms may, for example, be assembled to a bottom-less microplate where a measurement surface of the prisms forms the bottom of each well. A uv curable epoxy can be used to quickly adhere the prism shaped well bottom to the bottom-less microplate. In another embodiment, prisms can be molded from a polymer to form this microplate bottom. In yet another embodiment, the entire microplate with wells and prisms is molded in one unitary piece from a transparent polymer. Examples of moldable transparent polymers include polycarbonate, polystyrene, and polymethylmethacrylate (PMMA).

Samples provided in wells 52, 138 are typically mixtures of unknown or varying composition derived from biological sources such as blood, tissue, cells, etc. Samples may be known compounds, typically from a library of compounds which may bind to a biological entity. Samples may also be substances such as enzymes that have activity themselves. The sample may be dissolved or suspended in a media, where the media allows the sample molecules to diffuse with sufficient mobility to allow them to participate in an assay reaction. Media is often an aqueous saline buffer mixture but can also be other aqueous or non-aqueous solutions or mixtures.

One common type of sample that can be measured in reading instrument 73, 73' are samples that engage in specific binding. In these assays binding of one specific binding pair to another, such as antibodies with antigens, strands of nucleic acids with complementary nucleic acids, peptides, enzymes, glycans, and receptors with ligands, is measured. In one embodiment, one of the specific binding pair members is immobilized on a solid support, such as on well bottom prism measuring surface 72. A solution of sample in a media that may or may not contain the complementary binding pair is brought into contact with the immobilized binding pair member on well bottom prism measuring surface 72. If the complementary binding pair member is a constituent of the sample, a fraction of the binding pair members in solution will bind to their complementary immobilized binding pair partners on well bottom prism measuring surface 72. Such binding with the immobilized binding pair partner slightly changes the index of refraction of the material in contact with prism measuring surface 72. The assay measurement performed on the surface upon which the specific binding pairs have been immobilized will then detect a difference in index of refraction in measurements performed before and after introduction of the sample. The magnitude of the difference tells of the presence and also the concentration of pair members in the sample.

Members of a specific binding pair can be of the immune or the non-immune type. Immune specific binding pairs are exemplified by antigen/antibody systems or hapten/antihapten systems. The antibody member, whether polyclonal, monoclonal or an immunoreactive fragment thereof, can be produced by customary methods familiar to those skilled in the art. The terms immunoreactive antibody fragment or immunoreactive fragment mean fragments which contain the binding region of the antibody. Such fragments may be Fab-type fragments which are defined as fragments devoid of the Fc portion, e.g., Fab, Fab' and F(ab')2 fragments, or may be so-called "half-molecule" fragments obtained by reductive cleavage of the disulfide bonds connecting the heavy chain components of the intact antibody. If the antigen member of the specific binding pair is not immunogenic, e.g., a hapten, it can be covalently coupled to a carrier protein to render it immunogenic.

Non-immune binding pairs include systems wherein the two components share a natural affinity for each other but are not antibodies. Exemplary non-immune binding pairs are biotin-avidin or biotin-streptavidin, folic acid-folate binding protein, complementary probe nucleic acids, ligands-receptors, lectins-sugars, etc.

To facilitate the immobilization of specific binding pair members, cells, or cell fragments on well surfaces, microplate surfaces are commonly modified to improve adhesion properties. Improvement in adhesion has been found by irradiating the molded polymer of the plate or by coating the plate well surface with an additional polymer. An additional polymer layer can be provided by adding a mixture of monomer in well 52, 138 and allowing them to polymerize on surfaces of well 52, 138 to add another layer. The adhesion enhancing polymer formed could be a biological polymer, such as protein, or it could be an organic non biological polymer such polyacrylimide gel or dextran.

With or without surface modification, it is important to sterilize the wells for any assay application involving culturing or measuring live cells. A variety of cell phenomena can be measured with such an evanescent wave biosensor as shown in FIGS. 5a and 6, including cell growth, cell proliferation, cell death, and changes in cell morphology when cells are exposed to various stimuli such as cytokines, chemokines, or small molecules. For example, in one embodiment, living cells can be provided along a bottom surface of well on measuring surface 72. Media can then be provided to feed them or they may be hit with a toxic agent so the cells grow or shrink. Covering a higher percentage of the area of measuring surface 72 will cause a change in the measured index of refraction and a shift in position of image 139 on detector 40, as shown in FIG. 5a. The technique allows for detecting shrinkage in size of individual cells and reduction in area of measuring surface 72 covered as they die which would not revealed by techniques such as counting.

Assay measurement systems may use a single light source and detector pair to measure optical properties of one well of a microplate at a time. Several light source-detector pairs can be used in parallel to increase the number of wells read in a given time. Light source-detector pairs can be provided in a row of 8, 12, 16, 24, or another number to measure an integer factor of the wells in a column or row of a microplate. Such an integer factor is number that divides evenly in a row or column of wells in the microplate.

Either light source-detector pairs are moved or the plate is moved to provide relative movement there between to facilitate reading all of wells 52, 138 in microplate 50, 128.

Samples can be measured to provide before and after measurements or to provide for dynamically tracking during an assay. To get the starting value based on the index of material before binding begins, the first measurement may be made just before sample addition. Alternatively, the first measurement may be made at the same time as sample addition or just after sample addition. Many factors can influence the starting value of the index, including the addition of the sample itself before any binding happens. Because the sample and liquid added with the sample can affect the initial measurement, by doing the measurement at the same time or just after sample addition—but just before binding occurs—may provide a better initial measurement than doing the measurement before sample is added. Change in index from the initial value can then be attributed exclusively to binding.

The initial measurement provides optical properties of material adjacent measurement surface 72 or waveguide 134 of a given well before the reaction begins, including the refractive index of the bound material and of the buffer or media in which the assay is performed. If sample has been added, it may also provide the index of refraction of the sample in solution before it reacts with the bound material. The second measurement may be taken after a defined assay incubation period after sample has had a chance to react with bound material on the bottom surface of the well where the binding may affect optical properties of the bound material.

If the initial measurement is made before sample addition, one can wash out well 52, 138 and measurement surface 72 or waveguide 134 after the assay is complete and refill to make the final measurement with liquid identical to that used during the initial measurement before sample addition to eliminate the effect of sample and its liquid on the measurement.

The first measurement can then be subtracted from the second, and the difference is representative of the result of the assay, telling whether the binding material is present in the sample and its concentration.

Additional measurements can be made at intervals during the course of time to track binding of complementary species. These measurements can then be assembled into assay kinetic curves. Dynamically tracking thus produces more information from the assay. Depending on the frequency of measurement it may require that the incubation (which may take minutes or even hours) be performed while the microplate is located on the assay measurement system, limiting assay throughput. Before-after measurements have advantage in allowing the incubation to happen while microplate 50, 128 is removed from reading instrument 73, 73', allowing many more microplates to be measured with reading instrument 73, 73' during that period of time.

For some interferometer systems one may not be able to tell how much a fringe pattern shifted if one comes back later, so it may be desirable to dynamically watch the fringes move and count them as they go by. In such a case it will be desirable to incubate while tying up the reading instrument. The Brandenberg system illustrated in FIG. 6 with two slits has an advantage in allowing measurement without the need to count fringes going by.

The described methods of measuring refractive index of binding samples can also be applied to detect or measure concentration of other kinds of samples or to bulk liquid provided in multi-well structures, such as bulk liquid solutions with unknown concentrations. For example, the system can be used for detecting or measuring concentration of hundreds of samples of bulk liquids.

Another embodiment takes advantage of surface plasmon resonance (SPR) to measure refractive index of a material. SPR can also be used for sensing and measuring changes in refractive index and for label-less detection of assays, including binding assays. Surface plasmon resonance biosensors use surface plasma waves to probe biomolecular interactions occurring at the surface of a sensor. Early references to the SPR technique include Chabal et al., "Surface Electromagnetic Wave Launching at the Edge of a Metal Film," Appl. Phys. Lett., vol. 32, No. 2, January 1978, pp. 90–92; U.S. Pat. No. 4,844,613 Batchelder et al "Optical surface plasmon sensor device" first filed in 1985 ("the '613 patent"); and U.S. Pat. No. 4,997,278 Finlan et al. "Biological sensors" first filed in 1987 ("the '278 patent"), all of which are incorporated herein by reference. A current comprehensive survey of the technology can be found in Homola et al. "Surface Plasmon Resonance Biosensors" which is Chapter 7 of the book Optical Biosensors: Present and Future" (2002 Elsevier Science BV, ISBN: 0-444-50974-7, edited by Frances S. Ligler & Chris A. Rowe Taitt), incorporated herein by reference.

Figure 12:
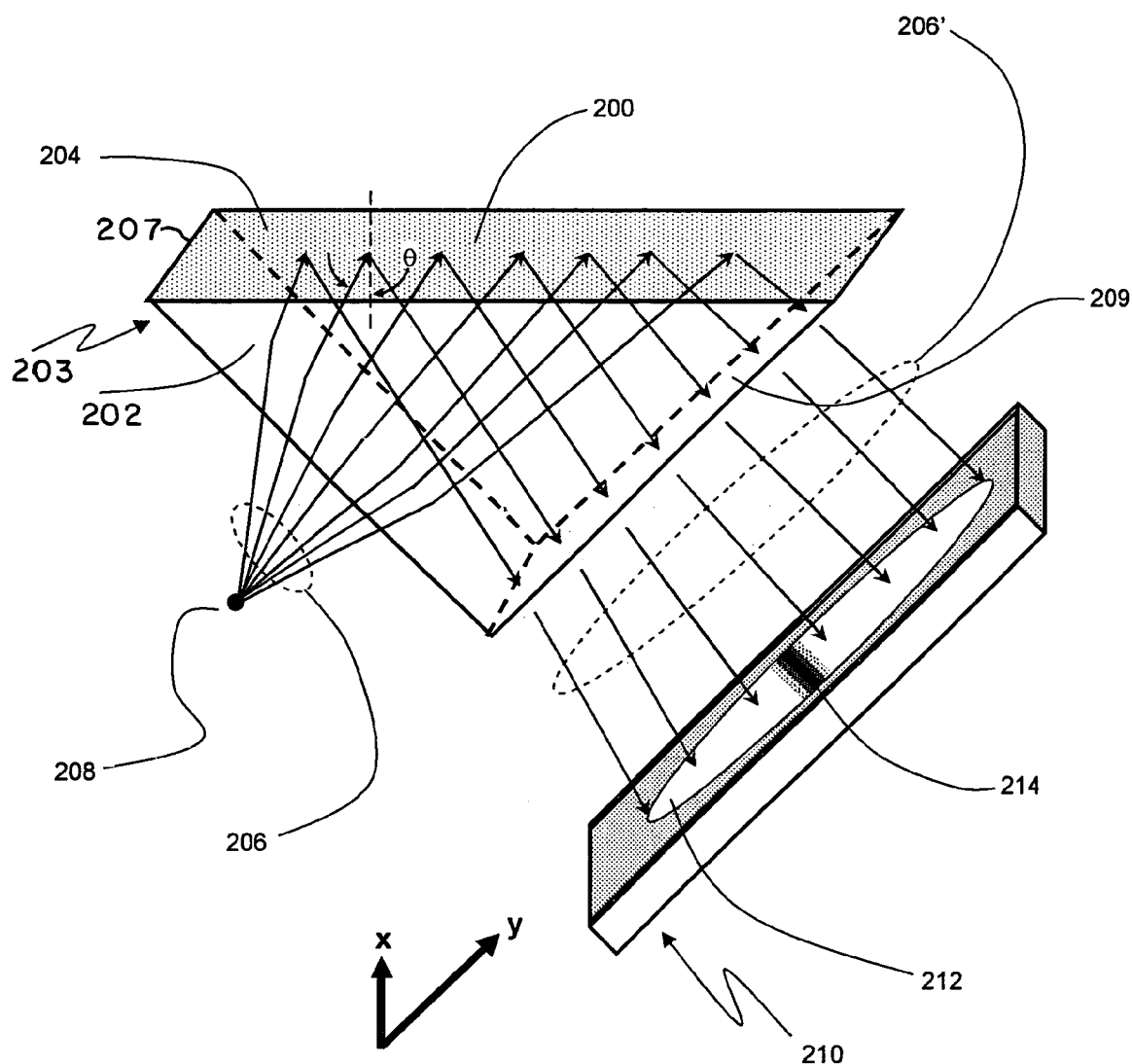
FIG. 12 is a three dimensional optical schematic of a prior-art SPR system.

SPR uses thin film of metal 200, typically gold about 50 nm thick, that is affixed to a planar interface surface of a dielectric optical element, such as prism 202, as shown in FIG. 12 to provide metal coated dielectric optical element 203. Gratings, waveguides and flat optical element coupled to a prism have also been used. Thin film of metal 200 is generally attached to optical measuring surface 204 by sputtering or another vacuum coating method. Fan of monochromatic interrogation light rays 206 are directed into entrance facet 207 of prism 202 from light source 208. Refracted interrogation rays 206 entering prism 202 impinge upon metal layer 200 coated on measuring surface 204 in a range of glancing incidence angles. Most of light rays 206 are reflected as exiting fan of light rays 206' which pass through exit facet 209 of prism 202 and shine on detector 210 to provide bright region 212. However, at a unique narrow range of angles for a particular wavelength, energy is transferred from interrogating light rays 206 into metal 200 by surface plasmon resonance. A pronounced reduction in reflection occurs at that narrow range of angles producing attenuated band 214 within bright region 212 on detector 210. The location of the dark SPR attenuation band 214 is detected and measured by detector 210 and electronic circuits to which it is connected. Movement of attenuation band 214 corresponds to refractive index changes in material on top of metal 200 on optical measuring surface 204.

Figure 13:
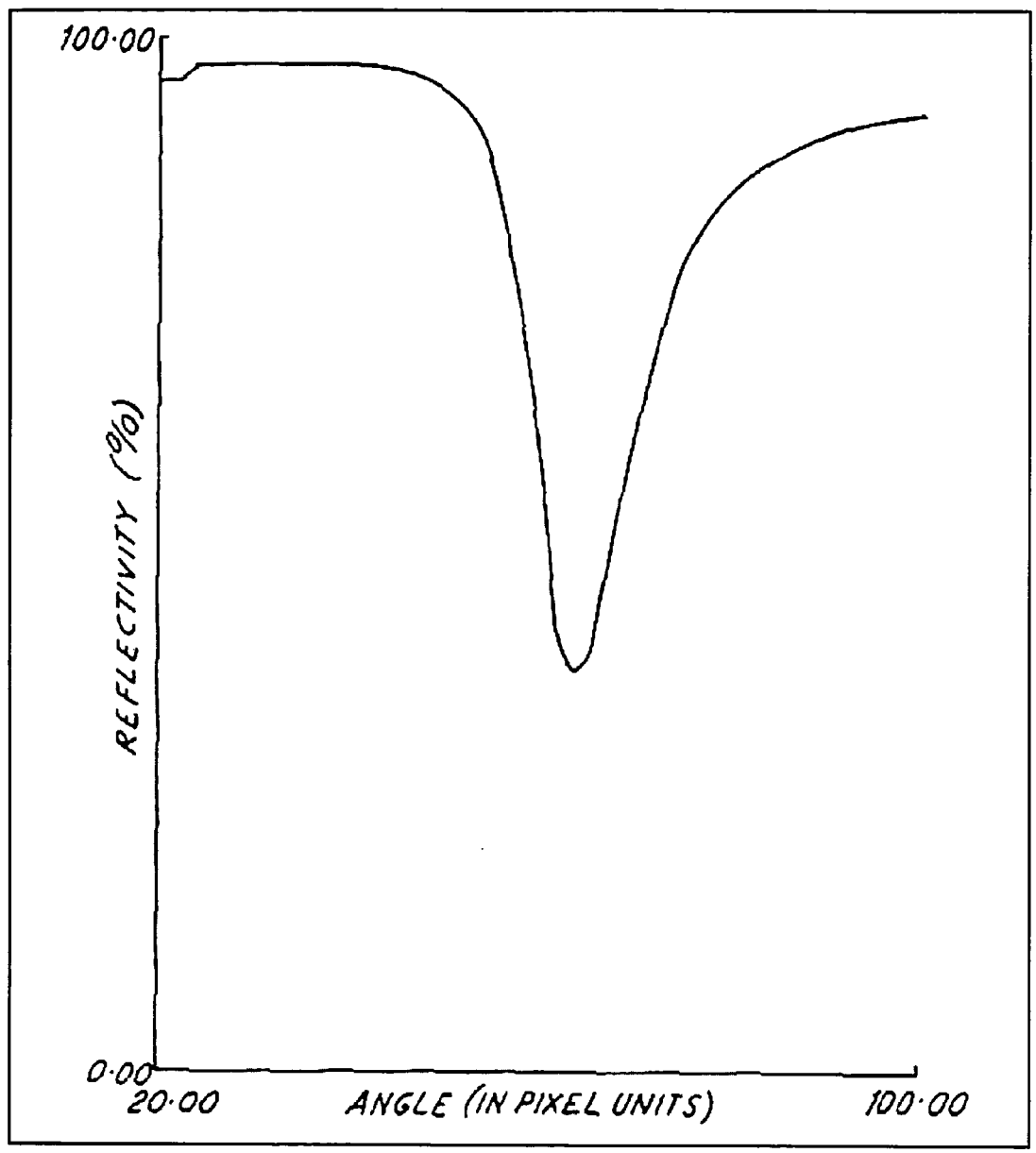
FIG. 13 is a reflectivity v. angle graph showing attenuation of light reflected at a narrow range of angles because of SPR.

An example of a reflection versus angle function of an SPR sensor is provided in FIG. 13, reproduced from the aforementioned '613 patent. The angle scale in FIG. 13 is shown in pixels for a particular implementation, magnifying the apparent width of the attenuation band. In angular space the attenuation band is typically less than 1 degree wide and most typically a small fraction of a degree.

Metal coated dielectric optical element 203 performs as a sensor of index of refraction of a material in intimate contact with metal 200 because the angle at which peak attenuation of a particular wavelength occurs depends on the index of refraction of that material in intimate contact with metal 200. The sensing range or distance away from the metal surface, determined by the distance by which the evanescent wave created by the resonance protrudes from the surface, is usually in the range of a few dozen to a few hundred nanometers, so the sensor is generally sensitive to the presence of materials within that range.

The observation and measurement of biological binding phenomena have been the primary application of SPR. The '613 patent describes coating the SPR sensor with antibody and detecting the binding of that antibody's antigen. An antibody and its respective antigen illustrate an example of a specific binding pair.

The sensitivity of assay detection with SPR can often be enhanced by the application of a thin polymer layer to the metal sensing surface, as described in U.S. Pat. Nos. 5,242,828 and 5,436,161, both incorporated herein by reference. The polymer layer is in the form of a porous gel, such as dextran or polyacrylamide gel a few hundred nanometers thick. The assay capture molecules are immobilized in this gel and the assay binding events occur in the gel. Suspension of a three-dimensional mass of biomolecules in the gel produces a larger SPR signal than a two-dimensional layer directly on the metal, as the protruding evanescent wave interacts solely with biomolecules rather than a combination of a few biomolecules immobilized to the flat sensor surface and a larger volume of liquid sample media above.

Metal 200 may be placed directly on the prism optic as shown in FIG. 12. Alternatively, as described by the '613 and '278 patents, metal may coat a flat measurement optical element which is then coupled to the prism by oil or another index-matching fluid. The '613 patent describes a right-angle prism, whereas the '278 patent uses a prism with cylindrical entrance and exit facets. Interrogation light rays 206 may be diverging, as in the '613 patent converging, as in the '278 patent, or collimated, as described in a paper by Emily A. Smith and Robert M. Corn, "Surface Plasmon Resonance Imaging as a Tool to Monitor Biomolecular Interactions in an Array Based Format," Applied Spectroscopy, 57 320A–332A (2003) ("the Smith reference"), incorporated herein by reference. The Smith reference describes an implementation of imaging SPR, in which a collimated interrogation beam is used and the angle of incidence is set so that all of the parallel reflected rays are partially attenuated by SPR. In this configuration this angle of incidence is set to be on a steep slope of the reflection v. angle curve shown in FIG. 13. Moving optics then scans that beam through a variety of angles, simulating a fan of rays. The changing angle of the collimated beam provides a time domain fan as opposed to a spacial fan of rays of FIG. 12. Reduction in intensity at the detector at a particular angle of incidence at a particular time provides the angle for attenuation by SPR. An imaging detector is not needed in this embodiment but the noise effects of speckle still add uncertainty to an angle measurement where one attempts to find a minimum optical power.

Detector 21 can be an imaging array detector, such as a CCD that captures the intensity of many small elements on its surface as pixel signals. In the measurement process a reference image is acquired before an assay. Then the sample is applied and allowed to incubate with material coating metal 200. One or more resultant images are then acquired. The reference image is subtracted from each result image, and the difference in brightness at each pixel is representative of the change in local refractive index, hence the local amount of binding of biomolecules.

Prior SPR assay implementations generally used flow cells for performing the assays in which a liquid sample flowed through a single vessel. Throughput was low because it took time to pump enough of a particular sample into the flow cell to clear material from a previous measurement and to stabilize a new concentration of material for the new measurement. An optical reading instrument was dedicated to a single flow cell. Such flow cells are particularly convenient for simplifying the analysis of binding affinity studies where the assay binding may significantly affect the concentration of analyte in the sample since the concentration of analyte in the material flowing through can be maintained constant. The flow cells are coupled to a SPR coupling prism and other instrument optics with an index-matching fluid interface. The flow cell can therefore be constructed separately from the prism as a consumable, allowing a relatively expensive glass prism to be permanently installed in the instrument and reused indefinitely.

However, flow cells are not convenient carriers or vessels for performing large numbers of assays, such as for biological screening. In many life science research or drug discovery settings, multiple samples need to be measured in a single session. For this reason, the molded microplate consisting of 96, 384, or 1,536 wells, described herein above, is commonly used for performing assays with signal-producing label chemistries such as fluorescence, luminescence, or radioactivity. The index-matching fluid used between the dielectric optical element and the measuring instrument of removable flow cells can also be an issue. The fluid must be applied consistently with no bubbles before applying the flow cell to the prism. Flow cell separation from the prism after measurement is difficult because of the need to overcome surface tension. Finally, the index-matching fluid must be cleaned from the instrument and from the flow cell after the assay to avoid assay contamination and the buildup of dust. Such processing of the index matching fluid slows down the measurements and reduce instrument throughput.

Because of the inconvenience of repeatedly installing and removing flow cells with an index-matching material for coupling, and also because of the expense of the flow cells, flow cells are often reused for multiple assays or tests by pumping clean material between assay samples or by pumping a sufficient amount of the next sample to clear an earlier sample. Researchers have validated processes that accommodate this re-use, but concerns about potential cross-contamination between samples need to be addressed with complex disassociation and washing protocols. As evidenced by the overall trend toward disposable labware in life science research, re-use of SPR flow cells provides a disadvantage.

Figure 14:
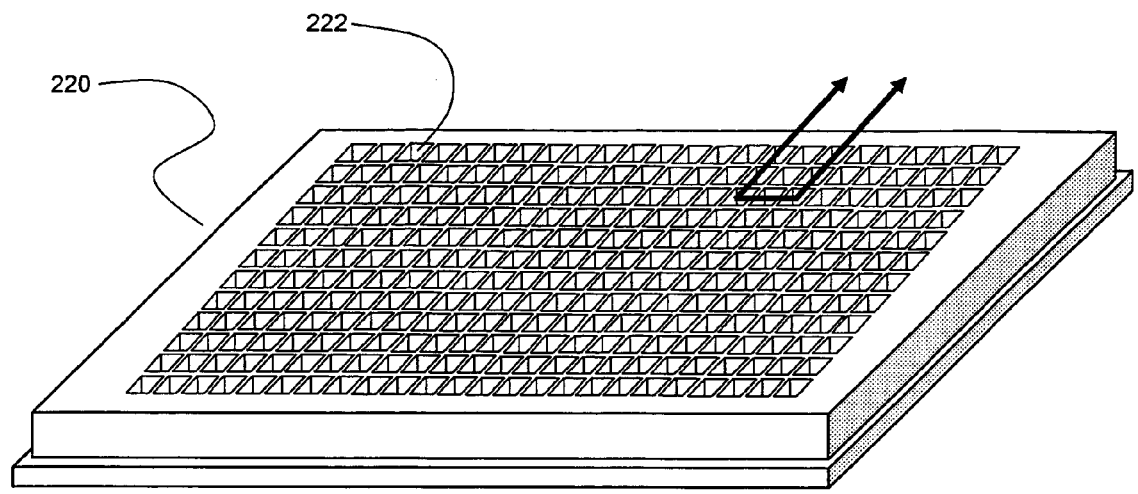
FIG. 14 is a three dimensional view of a 384-well unibody microplate illustrating another embodiment in which a thin metal coating is provided in wells of the microplate and wells have a prism-shaped well bottom.

The present teachings integrate SPR into wells and into microplate 220 having many wells 222, as shown in FIG. 14. Microplates with flat, transparent glass or plastic lower surfaces are commonly available. In one embodiment, such a microplate 220 is fabricated with a gold SPR coating on each well bottom and its flat lower surface is coupled to a prism with index-matching fluid, and used as a consumable SPR assay vessel. However, the operational difficulties of applying, removing and cleaning the index-matching fluid when installing and removing successive microplates remain, and such a system would not provide the high-throughput capabilities of labeled-assay microplate readers because it is slow to get rid of bubbles and dirt, and separating requires cleaning each time.

Therefore, in one embodiment, the disclosed methods and systems provide a measuring device for performing SPR assay measurements that combines the simplicity and low cost of the fixed-prism instrument, the throughput and ease of handling of standard-format microplates, the elimination of cross-contamination through inexpensive consumable sensors, and the convenience and high throughput stemming from the elimination of coupling using index-matching fluids or materials.

Figure 15:
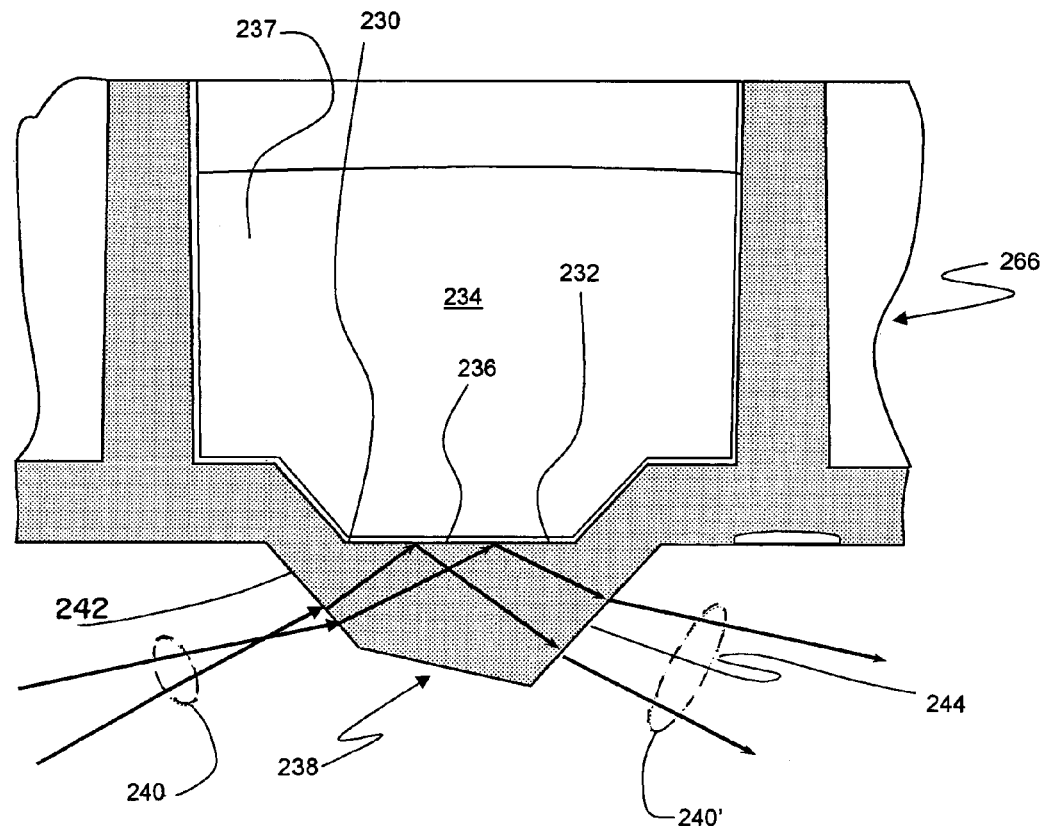
FIG. 15 is a cross sectional schematic of one well of the unibody microplate of FIG. 12, showing the metal coating and refractometer prism formed in a well bottom and the path of light through the prism.
Figure 16:
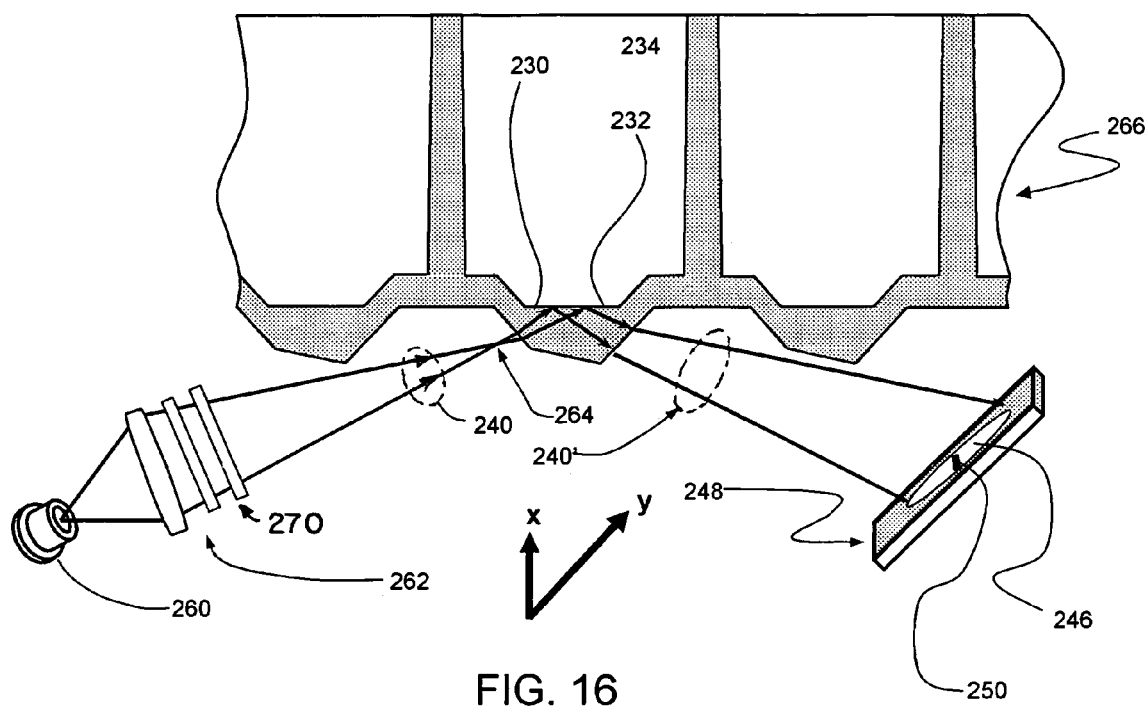
FIG. 16 is another cross sectional schematic of the unibody microplate of FIG. 12 with a light source, beam shaping optics, filter, and a CCD array detector.

In one embodiment a thin coating of metal 230, such as silver, gold, or another SPR-appropriate metal is coated on measuring surface 232 of well 234, as shown in FIGS. 15 and 16. Members 236 of a specific binding pair, such as antibodies, are coated on top of metal 230. Coating of members 236 may be directly or coating may be through a linker or a polymer (not shown) on metal 230. Thus, members 236 are available to capture their mating pair from sample 237 later applied to well 234. As described herein above, well 234 includes prism 238 integrated with well 234. Interrogation rays 240 enter prism 238 through facet 242 reflect from metal 230 and exit prism 238 from exit facet 244. Reflected rays 240' form illuminated area 246 on image-sensing detector 248. A relatively dark initial reference SPR attenuation band 250 is located somewhere within illuminated area 246. After sample 237 is placed in well 234 and reaches intimate contact with members 236 coated on metal 230 on measuring surface 232 causing binding pairs to form, the index of refraction in the evanescent wave detection zone at measuring surface 232 changes slightly causing the location of attenuation band 214 to move slightly. This movement is detected by image sensing detector 248, and electronics to which it is connected.

Light source 260 produces interrogation rays 240 and may be a laser, an LED, a superluminescent diode (SLD) or a light bulb. Diode lasers and LEDs both have high brightness and high electrical efficiency. Various wavelengths may be used, usually ranging from the visible to near infrared (500–900 nm). Lasers and SLDs are inherently monochromatic, whereas other light sources generally require wavelength filtering optics such as a narrowband filter to generate monochromatic interrogation rays.

Light from light source 260 is focused by beam shaping optics 262. Beam shaping optics 262 produces interrogation rays 240 having a range of angles including those for obtaining SPR excitation. The beam shape may be converging, diverging or collimated. In FIGS. 15 and 16, interrogation rays 240 are shown converging to focus 264 just before prism entrance facet 242. Focus 264 is a virtual point source from which fan of diverging interrogation rays 240 can be viewed to originate, as described herein above for the refractometry embodiment. As in that embodiment, this configuration is advantageous in that it allows light source 260 and beam forming optics 262 to be located further away from microplate 266, allowing freedom of movement for microplate 266 so that a single light source 260 and detector 248 can be moved with respect to microplate 266 to measure any well 234 in microplate 266. Collimated beam forming optics for imaging SPR can, of course, be placed far away from the structure. A collimated beam is moved through a range of angles to simulate a fan of rays as described herein.

Beam shaping optics 262 may be a conventional spherical lens. It can also be a cylinder lens or other anamorphic lens as described herein above for the refractometer embodiment.

Polarization optics 270 may also be incorporated into path of interrogation rays 240 depending on inherent polarization properties of light source 240. Interrogation rays 240 should be linearly polarized to provide the SPR effect.

While the disclosed methods and systems have been shown and described in connection with illustrated embodiments, various changes may be made therein without departing from the spirit and scope of the invention as defined in the appended claims.

The invention claimed is:

1. Apparatus for performing measurements on samples, said apparatus comprising
   a fixture;
   a support removably received in the fixture, said support having side walls and a bottom wall defining a multiplicity of sample-receiving wells arranged in columns and rows in a standard micro-plate format, said bottom wall also defining parallel truncated prisms each prism underlying an entire column or row of wells, each prism having a longitudinal axis, an exterior entrance surface and an exterior exit surface, said entrance and exit surfaces descending from an interior sensing surface located at the bottoms of the associated column or row of wells;

a linear array of light sources extending parallel to the prism axes for directing interrogating light rays into a selected one of said prisms through the entrance surface thereof so as to simultaneously interrogate any samples in a plurality of wells of the associated column or row of wells, said interrogating rays being reflected at the corresponding sensing surface and leaving the selected prism from the exit surface thereof as measuring rays;

a linear array of optical detectors extending parallel to the prism axes and paired with the array of light sources for simultaneously collecting said measuring rays and producing corresponding output signals indicative of refractive characteristics of any samples in said plurality of wells;

a positioning mechanism for moving the fixture and the paired source/detector arrays relatively, and a controller for controlling the positioning mechanism so that any samples in said plurality of wells can be measured simultaneously.

2. The apparatus defined in claim 1 and further including an output device responsive to the output signals for indicating the refractive indexes or index changes of any samples in said associated column or row of wells.

3. The apparatus defined in claim 1 wherein each light source provides an interrogating ray which converges to a point near the entrance surface so that the associated interrogating ray is diverging as it passes into the selected one of the prisms.

4. The apparatus defined in claim 1 wherein each light source produces polarized light and includes a wavelength filter so that the associated interrogating ray is monochromatic.

5. The apparatus defined in claim 1 and further including a thin metal layer coated on the sensing surface of each prism.

6. The apparatus defined in claim 5 wherein each prism is of a transparent polymer.

7. The apparatus defined in claim 6 wherein the polymer is one of the group consisting of polycarbonate, polystyrene, polysulfone and polymethyl-methacrylate.

8. The apparatus defined in claim 1 wherein the side walls and the bottom wall are molded as a unitary part.

9. The apparatus defined in claim 1 wherein each prism has a cross-section in the form of an inverted irregular trapezoid whose base corresponds to said sensing surface and whose opposite sides correspond to said entrance and exit surfaces, each prism also having a lowermost surface opposite the sensing surface which declines toward the exit surface.

10. The apparatus defined in claim 9 wherein said sides descend from the base at equal angles and the lowermost surface declines at an angle of about 100° relative to the base.

* * * * *